(12) United States Patent
Shoham et al.

(10) Patent No.: US 7,988,020 B2
(45) Date of Patent: Aug. 2, 2011

(54) WEARABLE DISINFECTING GEL DISPENSER

(75) Inventors: Gilad Shoham, Toronto (CA); Shmuel Shoham, Takoma Park, MD (US)

(73) Assignee: Medonyx Inc., Toronto, Ontario (CA)

( * ) Notice: Subject to any disclaimer, the term of this patent is extended or adjusted under 35 U.S.C. 154(b) by 1238 days.

(21) Appl. No.: 11/381,351

(22) Filed: May 2, 2006

(65) Prior Publication Data

US 2006/0289567 A1    Dec. 28, 2006

Related U.S. Application Data

(60) Provisional application No. 60/676,610, filed on May 2, 2005, provisional application No. 60/773,312, filed on Feb. 15, 2006.

(51) Int. Cl.
*B67D 7/84*    (2010.01)

(52) U.S. Cl. ...................................... 222/175; 224/148.4

(58) Field of Classification Search .................. 222/175, 222/183, 164–167, 100, 105, 106, 213, 214, 222/628, 192, 490, 491; 224/184.4–184.6
See application file for complete search history.

(56) References Cited

U.S. PATENT DOCUMENTS

| | | | |
|---|---|---|---|
| 4,634,022 A * | 1/1987 | O'Halloran et al. | 222/95 |
| 4,905,873 A * | 3/1990 | Loesel et al. | 222/181.2 |
| 5,927,548 A | 7/1999 | Vallaveces | |
| 5,941,426 A * | 8/1999 | Nagle et al. | 222/167 |
| 6,193,106 B1 | 2/2001 | Ho et al. | |
| 6,230,940 B1 * | 5/2001 | Manning et al. | 222/185.1 |
| 6,283,334 B1 | 9/2001 | Mahaffey et al. | |
| 6,695,174 B2 * | 2/2004 | Sørensen et al. | 222/214 |
| 6,951,295 B1 * | 10/2005 | Gaus et al. | 222/484 |
| 7,316,332 B2 * | 1/2008 | Powers et al. | 222/175 |
| 2004/0182897 A1 | 9/2004 | Andrews et al. | |
| 2004/0206776 A1 | 10/2004 | Awhrey et al. | |

OTHER PUBLICATIONS

PCT/US06/17009 Search Report dated Jan. 11, 2008.

* cited by examiner

*Primary Examiner* — Lien T Ngo
(74) *Attorney, Agent, or Firm* — Wilson Sonsini Goodrich & Rosati

(57) ABSTRACT

Provided is a wearable fluid dispenser including a reusable holster and a disposable cartridge containing fluid, wherein the cartridge is made of material having a flexibility higher than the flexibility of the holster, and wherein applying pressure to the cartridge allows dispensing onto the palm of the user's hand by way of increased pressure within the bottle resulting in the silicone valve opening and gel dispensing downwards.

14 Claims, 21 Drawing Sheets

Front oblique view

Rear oblique view

Figure 2  Front oblique view    Rear oblique view

FIGURE 9
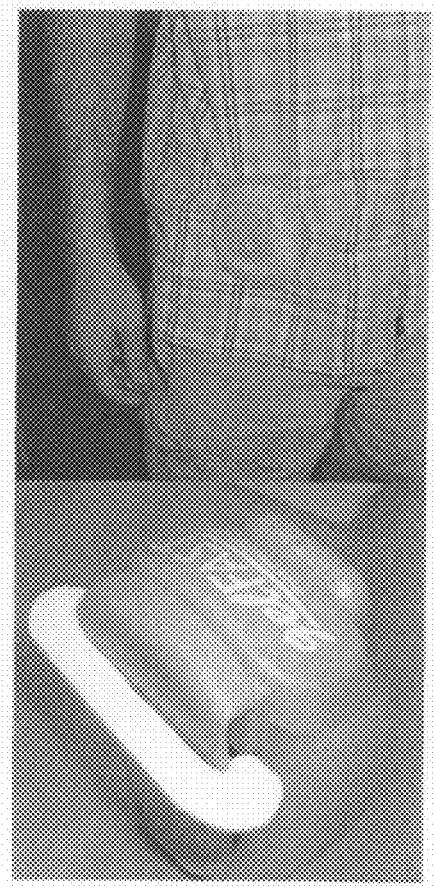
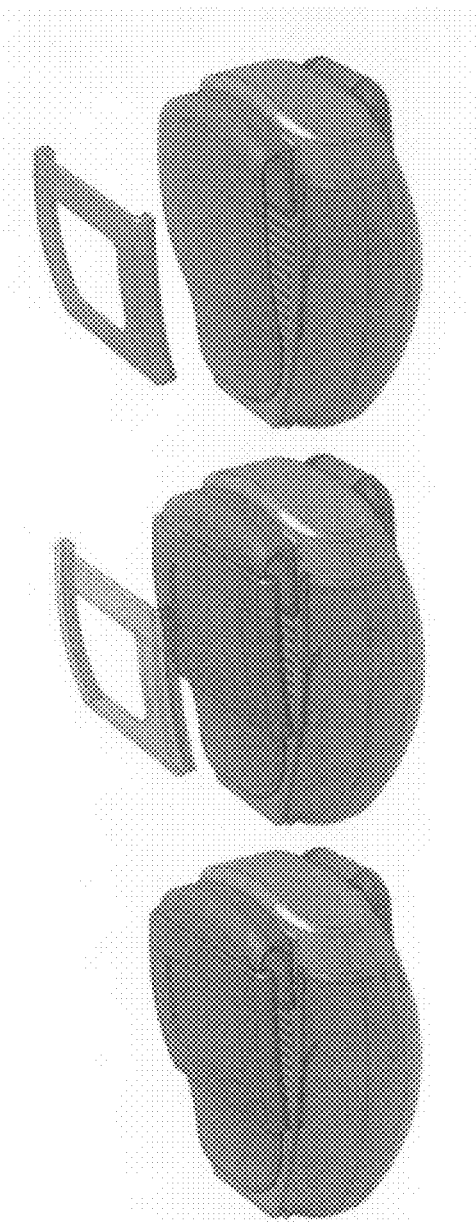

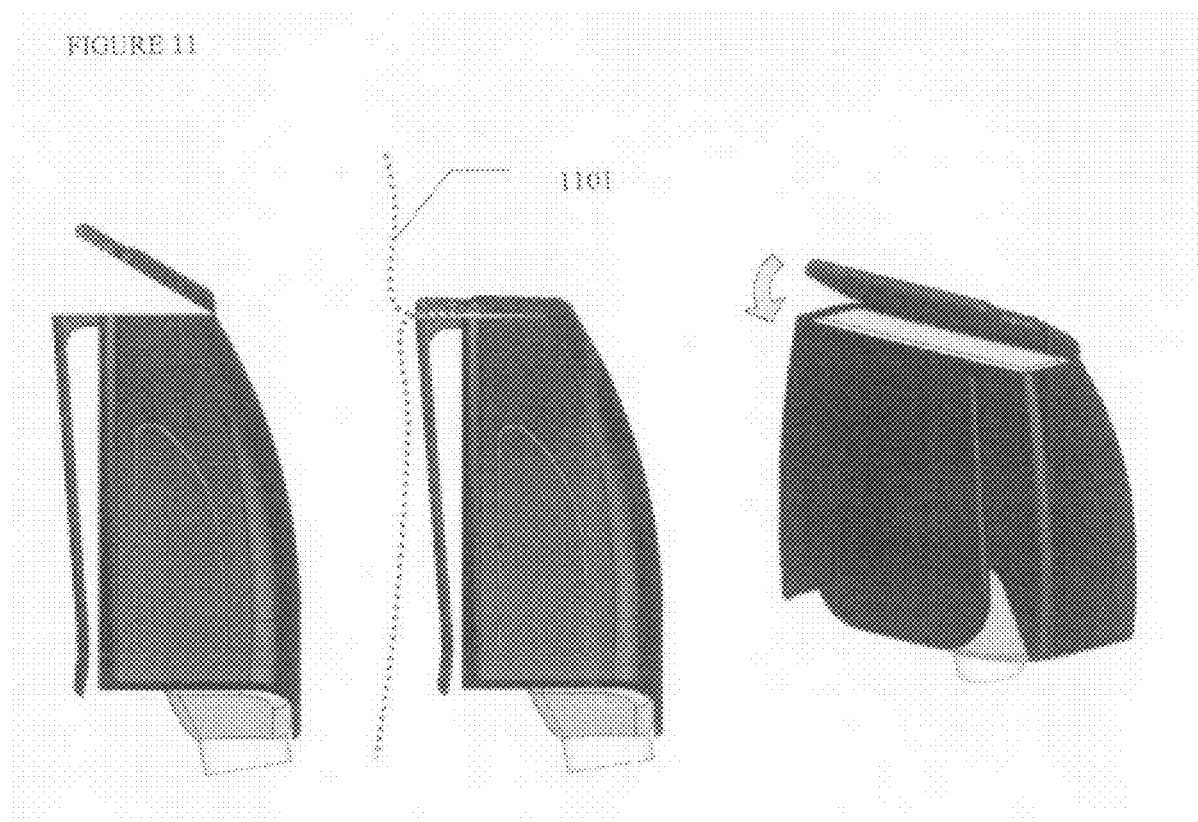

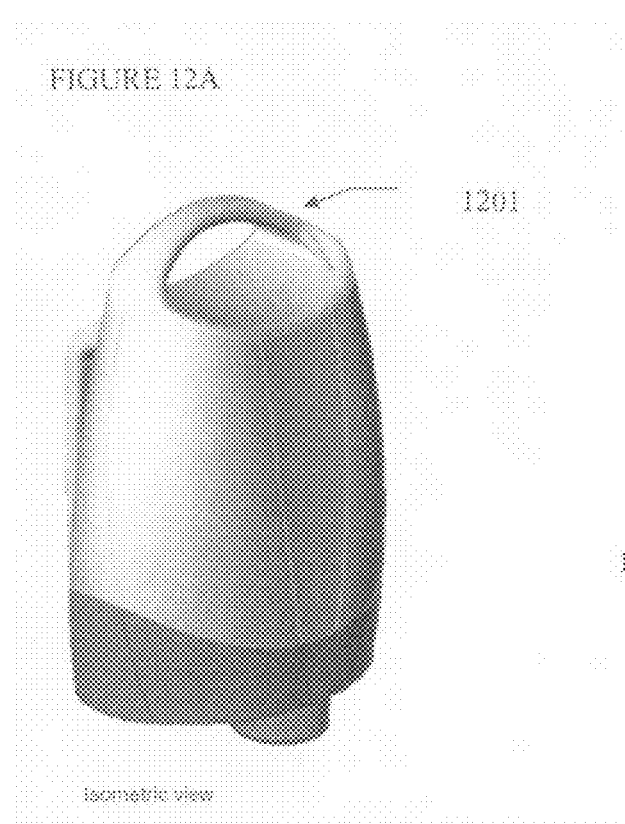
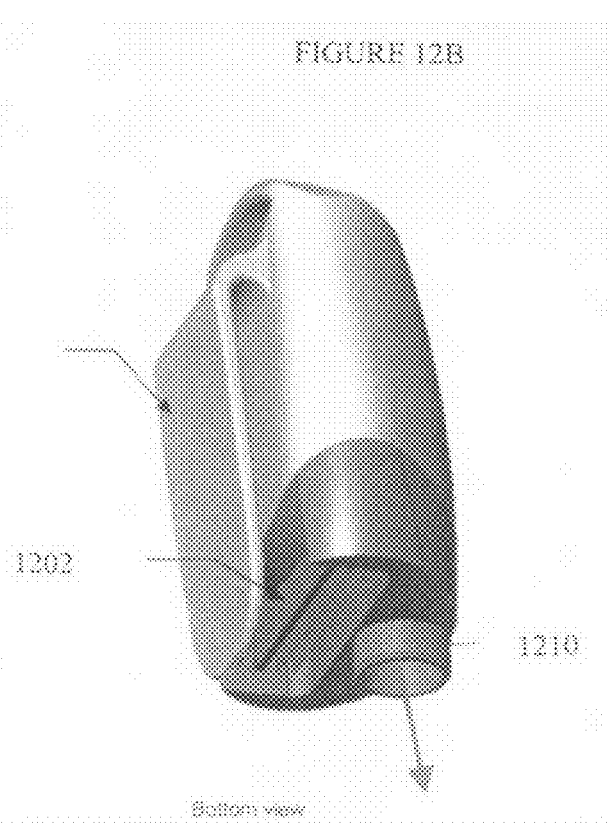

FIGURE 17
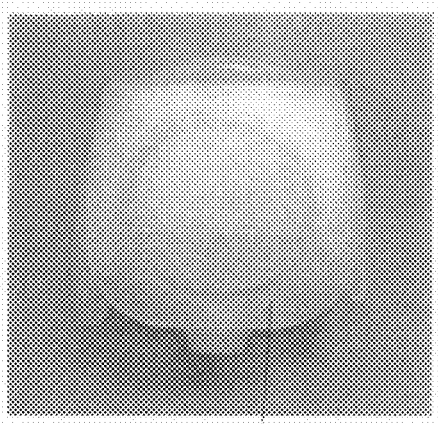
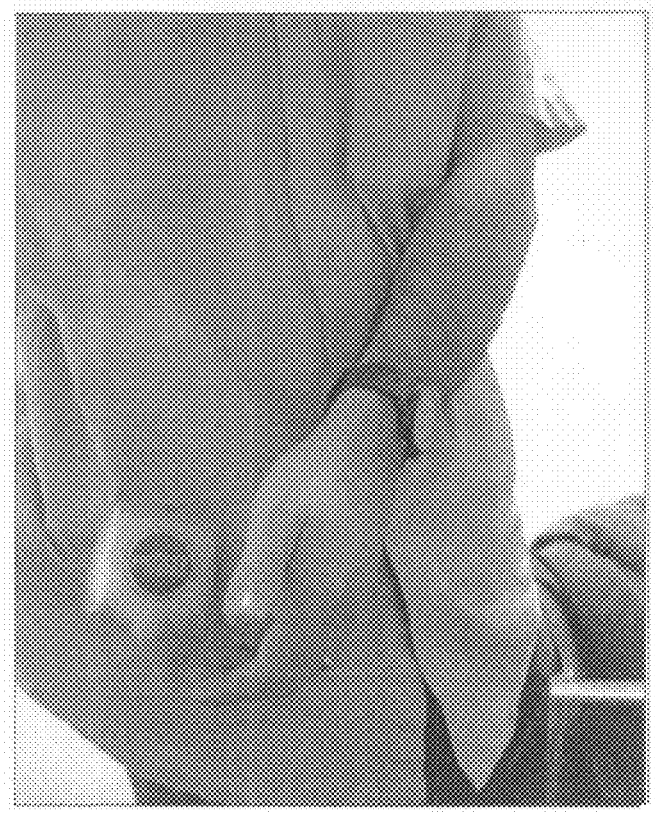
FIGURE 18
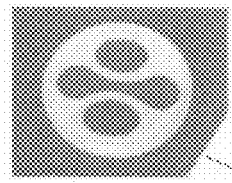
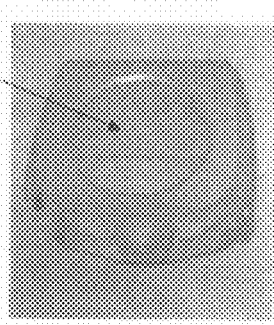
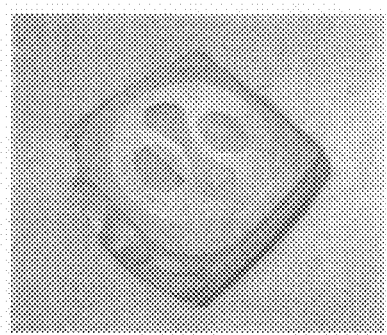

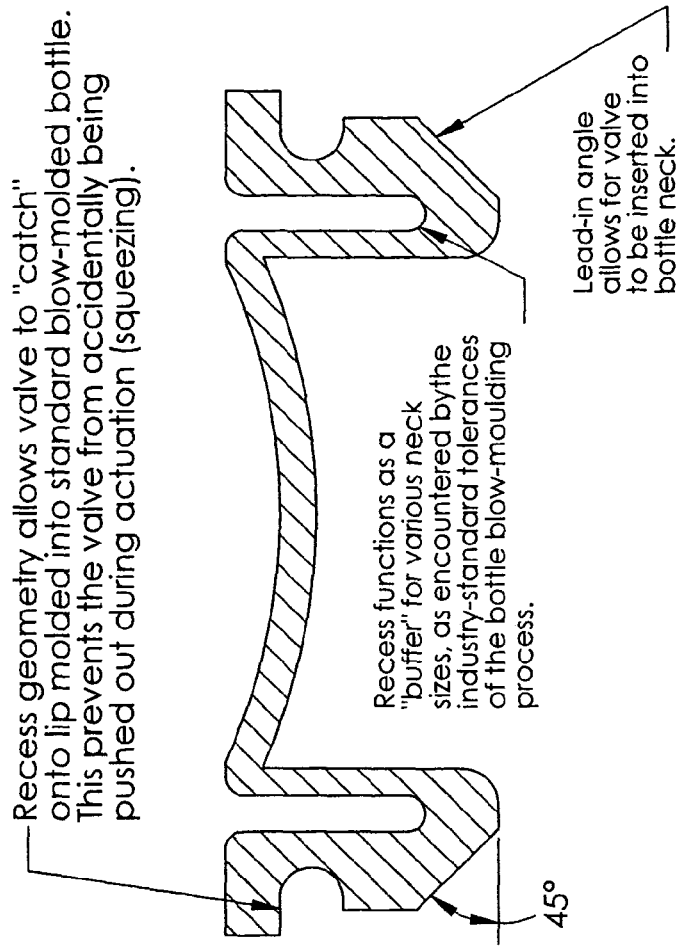
FIGURE 23
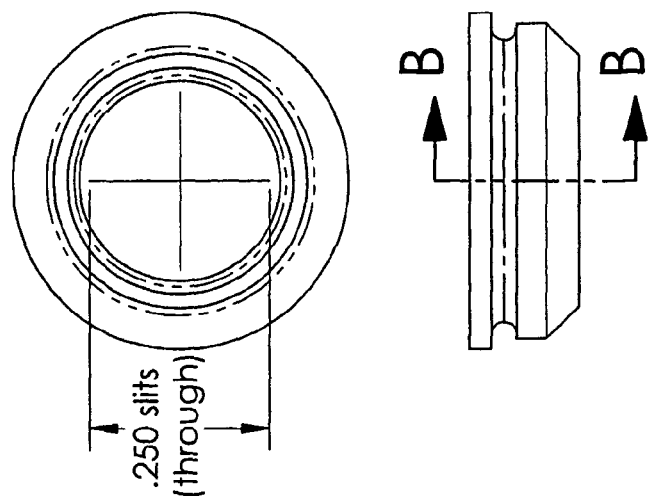

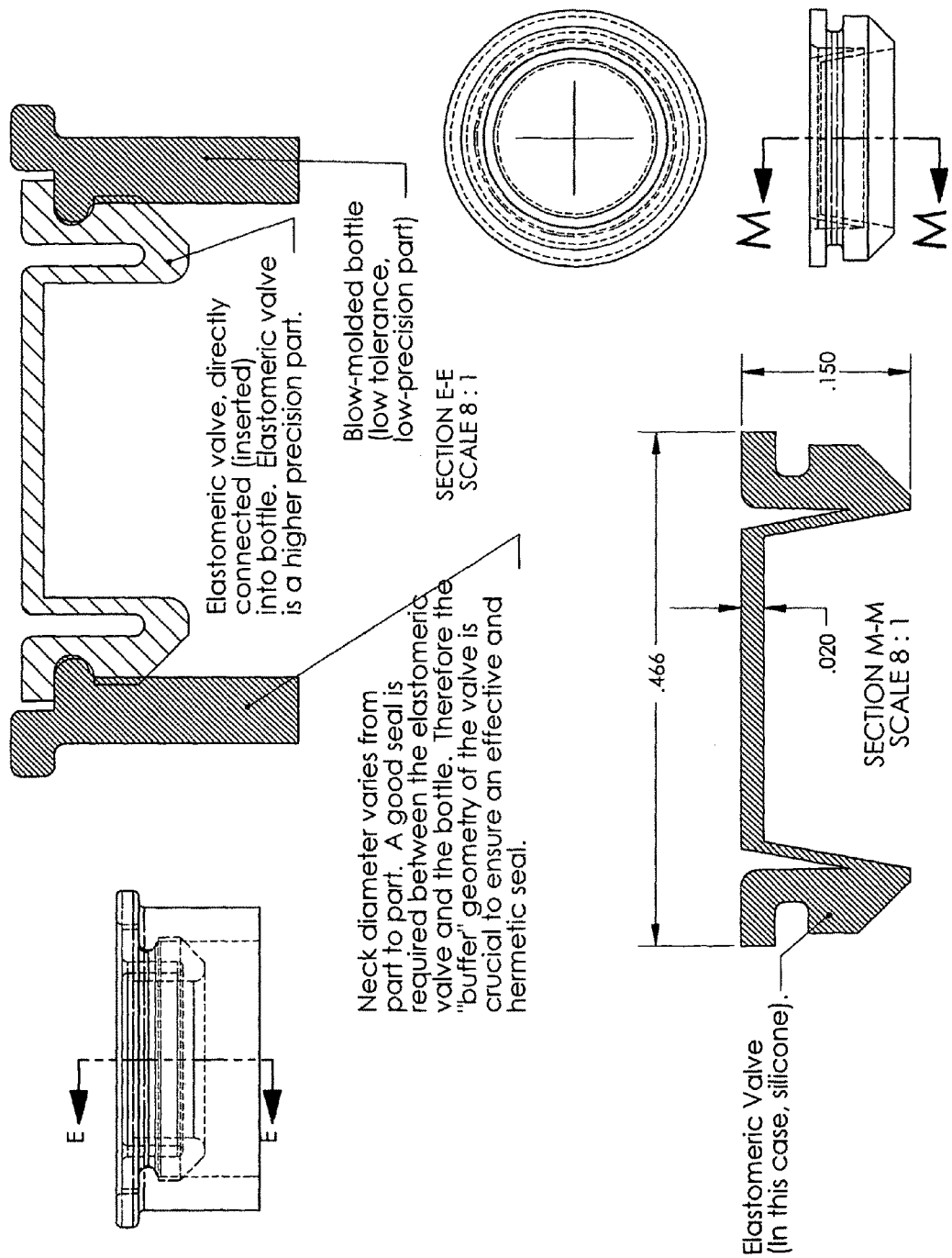

WEARABLE DISINFECTING GEL DISPENSER

CROSS-REFERENCE

This application claims the benefit of U.S. Provisional Application No. 60/676,610, filed May 2, 2005 and U.S. Provisional Application No. 60/773,312 filed Feb. 15, 2006. The contents of both provisional applications are incorporated herein by reference in their entirety.

BACKGROUND OF THE INVENTION

It is well understood that microbiological pathogens on the hands transferred to other body parts such as the mouth, nose and eyes are the primary cause of infectious disease in humans.

More importantly, in hospital settings, pathogens are moved from person to person and to/from inanimate objects (such as door knobs) to persons. In a hospital or similar environment, caregivers' hands are agents for transferring pathogens from and to patients, the caregivers themselves, and inanimate objects. The hands of heath care workers can carry disease-causing organisms from one patient to another. Accordingly, hand antisepsis before and after each patient contact is crucial to the prevention and control of nosocomial infection.

That improved hand hygiene can be achieved by using various hand sanitizing fluids is beyond question, the problems preventing this known technique from achieving a high degree of use (compliance) are equally understood as being time required and convenience of use. These same twin factors are true in the vastly greater pool of the general population, with the addition of a third very important factor—easy availability to achieve timely use, in a word, timeliness.

Antiseptic gels allow users to disinfect their hands without the use of running water. This convenience has allowed for their increasing popularity. In environments where frequent disinfection is desired—for instance in hospitals and other medical facilities, in food preparation areas, in animal handling situations, and other environments where humans are at risk of infectious contamination—this increased level of convenience affords the opportunity to allow for increased use and thus a reduced level of infection risk.

In order to achieve the frequency of use that infectious environments demand, it is important that users adopt the sequence of actions as a habitual second nature. A doctor or other care provider walking from patient to patient in a hospital, for instance, should automatically affect disinfection without even giving the matter a thought.

Accordingly, there is a need for a convenient, ergonomic wearable dispensing device that is designed for speed and ease of repeated use. Such device would promote the formation of a solid habit, a high degree of utilization, minimization of time taken for the disinfection action, and minimization of discomfort caused by a repeated action.

SUMMARY OF THE INVENTION

One embodiment provides a fluid dispenser comprising: a receptacle adapted to contain a fluid wherein the receptacle is removably attached to a clip for attaching the receptacle to the clothing of a person. The clip and receptacle are attached at one end through a hinge mechanism which allows the receptacle to be positioned in up-right and flipped down positions. The clip and receptacle are also attached at another end through a button, wherein the button is connected to a pumping unit attached to the receptacle, wherein the pumping unit enhances dispensing of fluid from the receptacle through an outlet aperture in the dispenser when the receptacle is in a flipped down position. The pumping unit comprises a locking mechanism which reduces or eliminates release of the fluid from the receptacle when the receptacle is in the upright position.

Preferably, the pumping unit comprises a redirect piping route to enhance dispensing of the fluid when the receptacle is in a flipped down position.

In another embodiment, the fluid dispenser further comprises an overcap button attached to the pumping unit, wherein the overcap button comprises a redirecting nozzle and an orifice which provides the aperture for dispensing the fluid from the receptacle when the button is actuated and the receptacle is in a flipped down position. In one embodiment, the overcap button has a sliding cover which covers the dispensation orifice when not in use.

In yet another embodiment the clip is attached to the receptacle through a hinge allowing the receptacle to be positioned in an upright or a flipped down position and the clip further comprises a bottle retained portion which allows the receptacle to be secured in the upright position.

In yet another embodiment the dispenser comprises a swivel body formed by the receptacle, the pumping unit and the overcap button, the swivel body being attached to the clip by a hinge integrally molded to the clip, whereby a user releases the swivel body from the upright position by pulling the swivel body away from the clip.

In a further embodiment the hinge mechanism and button are positioned to allow one-hand-action of the dispenser in rapid sequence through an unlocking of the dispensing function, a dispensing function, and a relocking of the dispensing function.

In a further embodiment, the hinge mechanism and button are positioned to allow a locked state wherein dispensation of fluid is substantially impeded and an unlocked state wherein dispensation is facilitated, wherein a user can switch between the locked and unlocked states with a one-hand-action sequence within two seconds or less.

In still another embodiment, a covering portion is positioned in the clip to prevent accidental discharge of fluid from the receptacle when the receptacle is in an upright position.

In yet a further embodiment, the receptacle comprises a hollow plastic component with threads to secure the pumping unit, threads to guide an overcap button in its travel, and threads to provide an angle-stopping feature when the receptacle is mated to the clip.

A further embodiment provides a method for dispensing an antiseptic gel or solution directly into the palm of a user comprising: (a) providing a fluid dispenser comprising: a receptacle adapted to contain a fluid wherein the receptacle is removably attached to a clip, wherein the clip is attached to a clothing of the user and the receptacle is positioned in an up-right position; (b) releasing the receptacle from the clip at a top end of the receptacle while a bottom end of the receptacle remain attached to the clip through a hinge mechanism; (c) bringing the receptacle to a flipped down position wherein the receptacle is at in a plane which is at an angle from the plane of the receptacle in the upright position;(d) dispensing the gel or solution into the palm of the user; and (e) bringing the receptacle to the upright position.

In one embodiment, step (d) comprises dispensing the gel or solution through a button attached to the receptacle and connected to a pumping unit, wherein the pumping unit enhances dispensing of the fluid from the receptacle through an outlet aperture in the dispenser when the receptacle is in the flipped down position and the pumping unit reduces or eliminates release of the fluid from the receptacle when the receptacle is in the upright position. Preferably, step (d) comprises redirecting the solution or fluid through a redirect piping route to enhance dispensing of the fluid when the receptacle is in the flipped down position.

In one embodiment steps (b) to (e) are performed in two seconds or less.

In another embodiment step (e) further comprises engaging a locking mechanism which locks the receptacle to the clip in the upright position.

In yet another embodiment the dispenser comprises a swivel body formed by the receptacle, a pumping unit and an overcap button, the swivel body being attached to the clip by a hinge integrally molded to the clip, wherein step (b) comprises releasing the swivel body from the upright position by pulling the swivel body away from the clip.

A further embodiment provides a method for dispensing an antiseptic gel or solution directly into the palm of a user from a fluid dispenser comprising: providing a fluid dispenser having a receptacle, a dispensing mechanism and a locking/unlocking mechanism, wherein the dispensing is performed in a one-hand-action of the user comprising rapid sequence of unlocking the dispensing function, bringing the receptacle from an upright position to a flipped down position, dispensing the gel or solution directly into the palm of the user through a pumping mechanism comprising a redirect route; bringing the receptacle to the upright position, and relocking of the dispensing function.

In one embodiment, the clip includes a slit for fabric retention.

Another embodiment provides fluid dispenser comprising an integrated clip and bottle comprising a molded flexible or collapsible portion which allows a user to dispense antiseptic agent by pressing on the flexible portion.

Another aspect provides a wearable fluid dispenser comprising a reusable holster and a disposable cartridge for providing a fluid, wherein the cartridge is made of material having a flexibility higher than the flexibility of the holster, and wherein applying pressure to the cartridge allows dispensing said fluid onto the palm of the user's hand by way of increased pressure within the bottle resulting in the silicone valve opening and fluid dispensing downwards.

In one embodiment, the cartridge comprises an integral nozzle facing downwards when the dispenser is in position for dispensing said fluid.

In another embodiment the holster comprises ears molded in the body of said holster for locking said cartridge inside said holster.

In a farther embodiment the holster comprises a frame geometry that allows attachment of the holster to a necklace that can be worn by the user.

In still a further embodiment the holster comprises a cutout portion that can be closed with a pug, wherein the dispenser can be attached to a user's clothing by positioning a piece of clothing between the cutout portion and the plug.

In another embodiment the holster is a plastic holster having two buttons which when depressed simultaneously allow release of the cartridge for replacement while preventing accidental release of the cartridge when in use.

In a further embodiment the cartridge comprises a valve fitted into a neck of said cartridge.

In one embodiment the valve comprises a membrane disposed between two lead-in portions.

In one embodiment the lead-in portions have angled or radial portions and lip portions which allow the valve to be secured to the neck of the cartridge.

In yet another embodiment the valve comprises a U shaped portion which provides a buffer space separating the membrane portion from the lead-in portions thereby allowing a high tolerance elastomeric valve to snap into a low tolerance low precision cartridge neck.

A further aspect provides a membrane comprising one or more slits which allow fluid in the cartridge to be dispensed through the valve when the cartridge is pressed.

In another embodiment the valve is fitted into a neck of said cartridge without the need for a seal piece.

Another aspect provides a wearable fluid dispenser comprising flexible and rigid regions, wherein the flexible region allows for dispensing fluid from the dispenser by applying pressure to the flexible region, and the rigid region prevents accidental dispensing of said fluid from the dispenser.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

FIG. 9 shows an embodiment with an additional clip component which attaches to belt clip to allow the dispenser to be attached to the clothing of a user without the need for a belt. The dispenser illustrated in the figure allows dual use with and without a belt.

FIG. 11 shows an embodiment incorporating a garment clip including a flap connected through a hinge to the main body of the clip whereby clothing of the user is positioned in the clip with the flap open, and snapping the flap closed allows for retention of the clip with the dispenser on the clothing of the user.

FIG. 12 shows an integrated clip and bottle for an entirely disposable dispenser. The dispenser includes a molded flexible or collapsible portion which allows the user to dispense antiseptic agent by pressing on the flexible portion.

FIG. 17 illustrates a mechanism for attaching the dispenser to other clothing articles.

FIG. 18 illustrates an exemplary embodiment employing a 2-part design to attach the dispenser to a clothing item. The 2-part design includes a clip a "plug" component which sandwich a piece of fabric.

FIG. 23 depicts a valve which snaps into the neck of a bottle without the need for additional seal disposed between the neck of the bottle and the valve FIG. 24 illustrates how the valve is directly disposed in the neck of the bottle.

DETAILED DESCRIPTION OF THE INVENTION

Provided herein is a convenient, ergonomic wearable dispensing device that is designed for speed and ease of repeated use. The device promotes the formation of a solid habit, a high degree of utilization, minimization of time taken for the disinfection action, and minimization of discomfort caused by a repeated action.

While the foregoing embodiments are described in conjunction with antiseptic agents, the devices and method described here in are applicable to dispensing other fluids, for example, sun blockers, tan lotions, moisturizing lotions, and the like. Use of those fluids in conjunction with the devices and methods described herein are fully contemplated and fall within the scope of the appended claims.

The dispensing device allows the user (e.g., a hospital professional) to avoid the creation of defensive habits, by providing a dispensing device which minimizes the risk of accidental dispensation, leaks, breakage, and over-dispensation. The device is advantageous in that the benefits thereof can be obtained without requiring any significant modification of behavior from the wearer. The exterior of the device remains clean even immediately after dispensation. The wearer with a solid formed habit can use the dispenser frequently while barely being cognizant of this Provided herein are multiple embodiments that allow the user to achieve the above objectives based on the concept of a dispenser with a design that admits a locked state—where dispensation is substantially impeded—and an unlocked state—where dispensation is easy—with a one-hand-action sequence cycling through these states.

As used herein the terms "antiseptic fluid" refers to all forms of an antiseptic agent including without limitation appropriate cleansing foam including aerosolized foam, gel, suspension, dispersion, or solution or any other agent capable of being dispensed through an orifice of a dispenser as described herein. While some embodiments are illustrated based on a gel antiseptic agent, those of skill in the art will have no difficulty applying those embodiments to other forms of antiseptic agent as appropriate. All forms of antiseptic agent that can be used in conjunction with the devices described herein are contemplated and are within the scope of the claims below.

Figure 1:
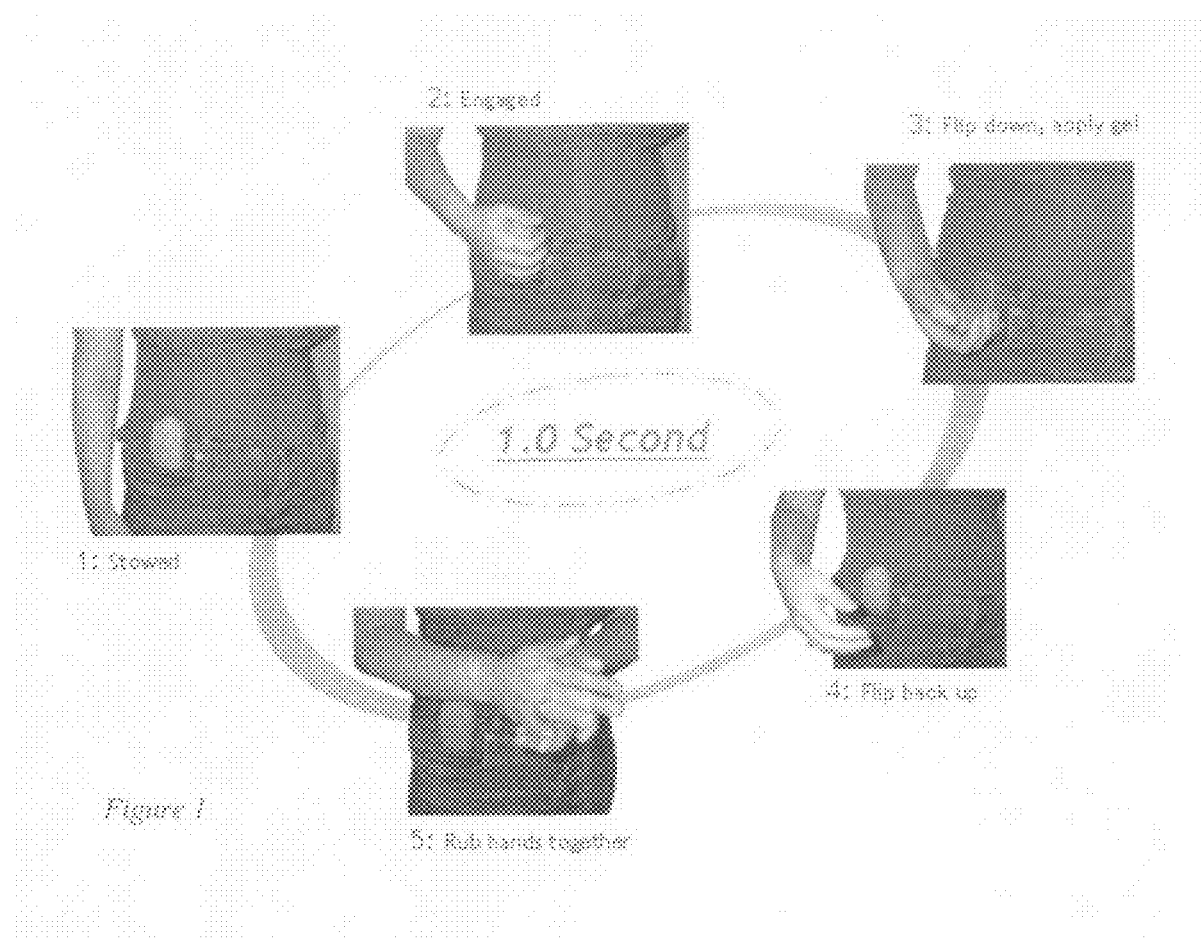
FIG. 1 illustrates the one hand dispensation concept.

FIG. 1 illustrates one embodiment for a dispenser based on a one hand dispensation concept.

In position 1, a dispensing device is secured to the belt of the user. The dispensing device is in an upright locked position. In position two, the user is shown to initiate the dispensation process by unlocking a receptacle which contains the aseptic gel or solution to be dispensed in the palm of the user. In position 3, the receptacle is positioned in a flipped down position ready to apply gel or solution directly into the palm of the user. At this time a pumping unit is actuated and aseptic gel or solution is released directly in the palm of the user. In position 4 after the release of aseptic gel or solution in the palm of the user, a finger (for example a thumb) of the same hand (in this case the right hand of the user) is used to bring the receptacle to an upright position. The receptacle is pressed into a clip thereby locking the receptacle back into a position wherein dispensation is substantially impeded until the receptacle is unlocked for another cleaning sequence. Position 5 shows the user rubbing the hand on which the aseptic gel or solution was dispensed (here the right hand) with the other hand of the user (here the left hand). Rubbing the two hands allows the aseptic gel or solution to clean the user's hands. The sequence illustrated in position 1 to 4 of FIG. 1 can be completed in two seconds or less, which makes the device provided herein greatly efficient which in turn allows seamless cleaning at all times and in all locations.

By way of illustration, FIG. 1 shows how a wearable dispenser can be used. FIG. 1, illustrates one embodiment with a wearable dispenser which utilizes a belt clip with a flip-open action as the locking/unlocking mechanism and a pump button for dispensation. The opening action insures that dispensation takes place only upon activation and directly into the hand that affect the opening. In a device according to one embodiment, dispensation of the gel or liquid contained in the bottle occurs only when the bottle is unlocked and disengaged from the locked upright position. After the bottle is unlocked and disengaged, the bottle can be brought to an angle from the upright position. The measure of the angle formed between a plane of the bottle in an unlocked position and the plane formed by the bottle in a locked upright position may be between about 2 and about 135 degrees. The steps illustrated in FIG. 1 are summarized as follows:

Steps:
1. Shows unit in "stowed" position—gel cannot be dispensed with the bottle in an upright locked position. There is a mechanical lock on the belt-clip, which both retains the bottle upright and prevents the button from being depressed accidentally.
2. The user grips and pulls the bottle away from the clip.
3. The user "flips" down the bottle. The belt-clip, which secures the apparatus to the user, is still in its original (and only) position. The bottle pivots down to a horizontal position via hinge geometry between it and the clip component. As indicated above, the horizontal position illustrated here shown only one embodiment. The gel can be dispensed when the bottle is unlocked and disengaged from the clip with a wide range of measurement for the angle formed by the plane of the bottle in an unlocked position and the plane containing the clip. After the bottle is unlocked and tilted away from the upright position, the user now presses a button, which dispenses a gel through an orifice on the button. In one embodiment, the gel is only dispensed downwards relative to the ground, and the ergonomic design of the unit ensures that the proper amount of gel is dispensed in the palm of the hand of the user, and not between fingers or other unwanted locations.
4. The user returns the unit to its upright and stowed position, ready for another use.
5. The user now rubs hands together, ready to continue with their day.

Accordingly, an embodiment provides a method for dispensing an antiseptic gel or solution directly into the palm of a user comprising: (a) providing a fluid dispenser comprising: a receptacle adapted to contain a fluid wherein the receptacle is removably attached to a clip, wherein the clip is attached to a clothing of the user and the receptacle is positioned in an up-right position; (b) releasing the receptacle from the clip at a top end of the receptacle while a bottom end of the receptacle remains attached to the clip through a hinge mechanism; (c) bringing the receptacle to a flipped down position wherein the receptacle is in a plane which is at an angle from the plane of the receptacle in the upright position;(d) dispensing the gel or solution into the palm of the user; and (e) bringing the receptacle to the upright position.

In one embodiment, step (d) comprises dispensing the gel or solution through a button attached to the receptacle and connected to a pumping unit, wherein the pumping unit is connected to a piping mechanism which enhances dispensing of the fluid from the receptacle through an outlet aperture in the dispenser when the receptacle is in the flipped down position while the locking mechanism reduces or eliminates release of the fluid from the receptacle when the receptacle is in the locked upright position. Preferably, step (d) comprises redirecting the solution or fluid through a redirect piping route to enhance dispensing of the fluid when the receptacle is in the flipped down position.

In one embodiment steps (b) to (e) are performed in two seconds or less.

In yet another embodiment the dispenser comprises a swivel body formed by the receptacle, a pumping unit and an overcap button. In one embodiment, the swivel body is attached to the clip by a hinge integrally molded to the clip. Step (b) comprises releasing the swivel body from the upright position by pulling the swivel body away from the clip.

A further embodiment provides a method for dispensing an antiseptic gel or solution directly into the palm of a user from a fluid dispenser comprising: providing a fluid dispenser having a receptacle, a dispensing mechanism and a locking/unlocking mechanism, wherein the dispensing is performed in a one-hand-action of the user comprising rapid sequence of unlocking the dispensing function, bringing the receptacle from an upright position to a flipped down position, dispensing the gel or solution directly into the palm of the user through a pumping mechanism connected to a piping redirect route; bringing the receptacle to the upright position, and relocking of the dispensing function.

FIGS. 2-7 show different views of a device according to selected embodiments.

Figure 2:
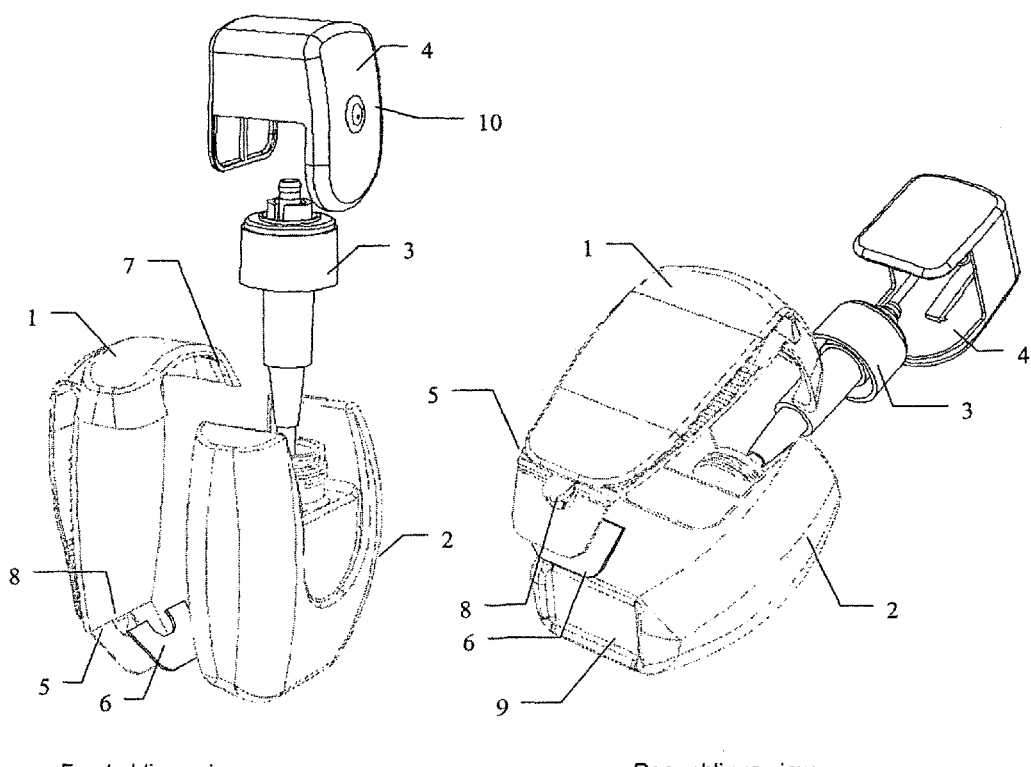
FIG. 2 shows front oblique and rear oblique views for one embodiment of the dispensing device and a clip.

FIG. 2 shows front oblique and rear oblique views for one embodiment including a Clip (1) which can be attached to a user clothing item such as a belt. Clip (1) can be worn on a belt or pant waist, coat pocket, or any other convenient location. This part remains on the person statically. In some embodiments, the clip includes features that allow it to mate to the bottle (2) and provide a hinging capability via a "hinge", as well as to hold the bottle upright when in stowed position via "retention clip" or cover geometry. In some embodiment, the clip limits the angle at which the bottle (2) and related assembly will reach when in the "open" position, through the use of a small protrusion (8) on the bottom of the part.

In some embodiments, the bottle (2) can be a hollow plastic component, with features engineered into it to accept pump engine or pumping unit (3), to guide overcap button (4) in its travel, and to provide an angle-stopping feature when mated to the clip (1).

Pump engine or pumping unit (3) includes a pump mechanism, a means of attachment to the bottle (2). In some embodiments a threaded neck (threads not illustrated in this picture) serves as the means of attachment.

In some embodiments overcap button (4) acts as a large, ergonomic button, and also as a "redirecting nozzle"—whereby antiseptic gel is routed through an internal channel out the orifice (10) in the front exterior of the part. In preferred embodiments, the gel or solution ultimately exits from this component onto the hand of the user. This piece snaps onto the pump engine or pumping unit (3).

I some embodiments adhesive tab (6) is provided as a small piece of double-sided adhesive tape utilizing a high bonding strength adhesive to fasten the bottle component (2) to the hinge flap of the clip (1).

Clip (1) includes retention clip geometry (7) which allow the bottle 2 to remain locked within the clip and cover the overcap (4) thereby preventing accidental release of the antiseptic agent when the dispenser is in the upright locked position. The user can unlock the dispenser by pulling the bottle away from the clip. The dispenser is relocked after antiseptic agent is dispensed by snapping the bottle back in the upright position. As discussed below in connection with FIG. 9, other embodiments are disclosed herein for locking the bottle within the clip and allowing for hinge movement for the bottle to be positioned in a flipped down position.

In one embodiment the locking function is accomplished by covering the overcap with a hood or bottle retaining portion of the clip (7). Covering the button actuator with the shoulder, hood or cover of the clip puts the button temporarily out of reach of the user, disabling its use and preventing accidental discharge of the antiseptic agent.

In one embodiment the bottle has on it a shape that mates up firmly with the clip. In this case the bottle has a dovetail-type protrusion on the bottom, whereas the clip has a cavity of roughly the same dimensions, resulting in a secure fit between the components.

Figure 3:
FIG. 3 is an illustration of unit according to one embodiment, assembled in an upright (stowed) position.

FIG. 3 is an illustration of unit according to one embodiment, assembled in an upright (stowed) position. The figure shows a preferred orifice location which allows dispensation directly in the palm of the user. When the unit is in stowed position, the button cannot be accidentally depressed due to protective covering geometry of the clip component.

Figure 4:
FIG. 4 provides an illustration of an embodiment with an assembled dispensing unit in a downwards or flipped down ready-to-dispense position.

FIG. 4 provides an illustration of an embodiment with an assembled dispensing unit in a downwards or flipped down ready-to-dispense position. Orifice is now positioned directly where the center of the user's palm will be.

Figure 5:
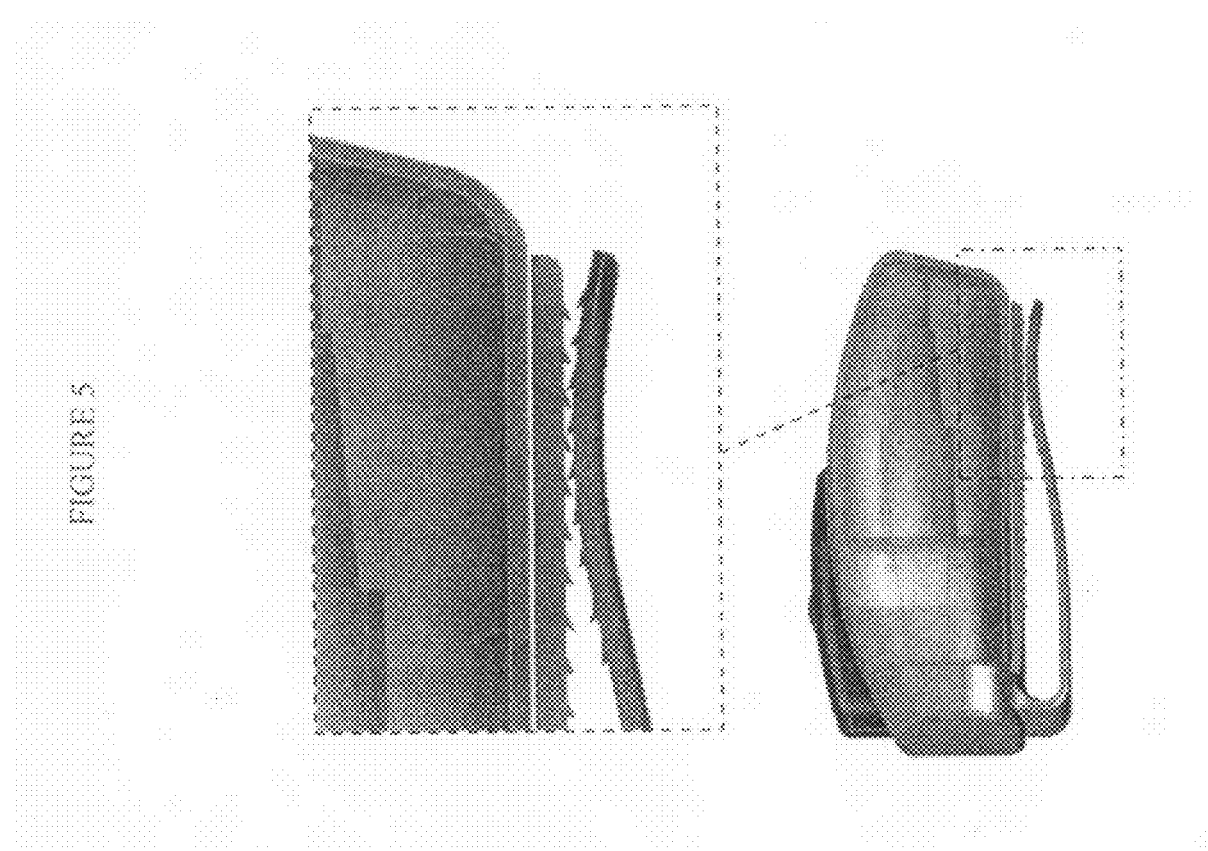
FIG. 5 shows one embodiment wherein the clip (1) includes directionally biased serrated geometry to optimize location retention and enhance the functionality of the clip component.

FIG. 5 shows one embodiment wherein the clip (1) includes serrated geometry to optimize location retention and enhance the functionality of the clip component.

Referring back to FIGS. 1 and 2 an embodiment for using the dispensing device step by step usage description: Entire unit is attached to user's belt using Clip (1)

User's hand grasps "swivel body" (2,3,4)

User pulls "swivel body" (2, 3, 4) away from Clip (1), pivoting at the "Hinge" (5), integrally moulded to Clip (1), thus releasing the Clip's (1) Position Locking Mechanism (7) (whose function is to maintain the "closed" orientation of the "swivel body" (2, 3, 4). [Clip (1) is fixed to Bottle (2) by means of the adhesive tab snap-on (6).]

Unit is pivoted until Pivot Stop feature is engaged (8), whereby a small flap of material existing on the Clip (1) makes contact with the bottom mating surface (9) of the Bottle (2).

Overcap button (4) is pressed by user's hand to activate pump (3) and release gel stored in Bottle (2) through Nozzle Orifice (10) in the Overcap button (4) onto palm of user's hand.

Swivel Body (2, 3, 4) is flipped back into stowed position by fingers of user's hand, thereby re-engaging the Locking Mechanism (7)

Hands are rubbed together for several seconds to allow gel to act in antimicrobial fashion.

Accordingly, provided herein is a dispenser device, which includes a fluid dispenser comprising: a receptacle adapted to contain a fluid wherein the receptacle is removably attached to a clip for attaching the receptacle to the clothing of a person. The clip and receptacle are attached at one end through a hinge mechanism which allows the receptacle to be positioned in up-right and flipped down positions. The clip and receptacle are also attached at another end through a locking feature formed in the top portion of the clip. The dispenser includes a button, wherein the button is connected to a pumping unit attached to the receptacle, wherein the pumping unit enhances dispensing of fluid from the receptacle through an outlet aperture in the dispenser when the receptacle is in a flipped down position. The clip's locking mechanism reduces or eliminates release of the fluid from the receptacle when the receptacle is in the locked upright position.

Figure 6:
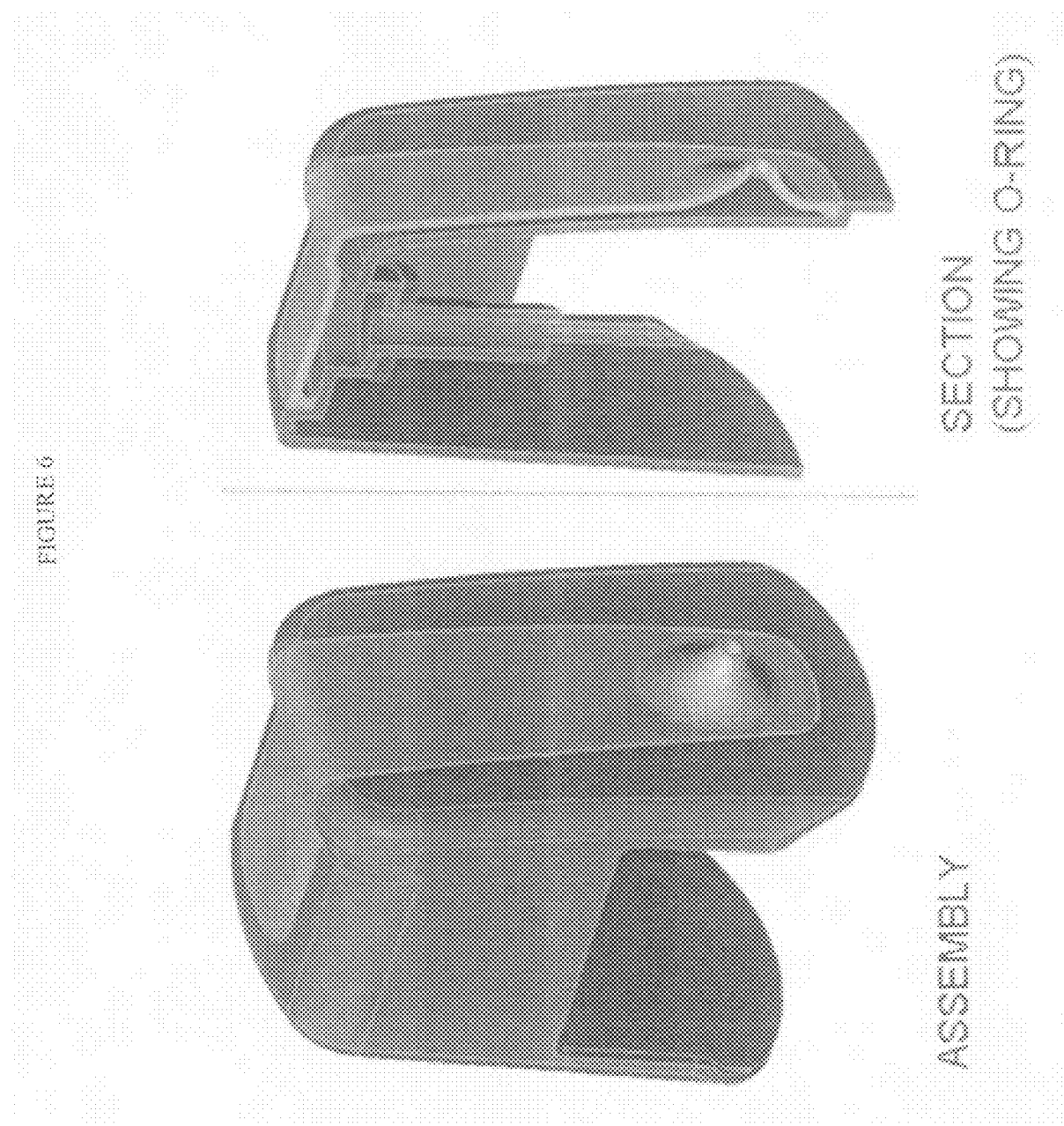
FIG. 6 shows an embodiment with two piece overcap with gel redirect "piping route" allowing gel to dispense in palm of users hand.

Preferably, the pumping unit communicates with a redirect piping route to enhance dispensing of the fluid when the receptacle is in an unlocked or a flipped down position. FIG. 6 shows an embodiment with 2-part overcap with gel redirect "piping route" allowing gel to dispense in palm of users hand. A main part of the overcap allows the pumping of the antiseptic agent from the bottle through a larger orifice. A second part of the overcap is fitted into the first part and provides a piping mechanism which brings the antiseptic agent into a smaller orifice for dispensing the antiseptic agent. The smaller orifice allows for acceleration in discharging the antiseptic agent.

Figure 7:
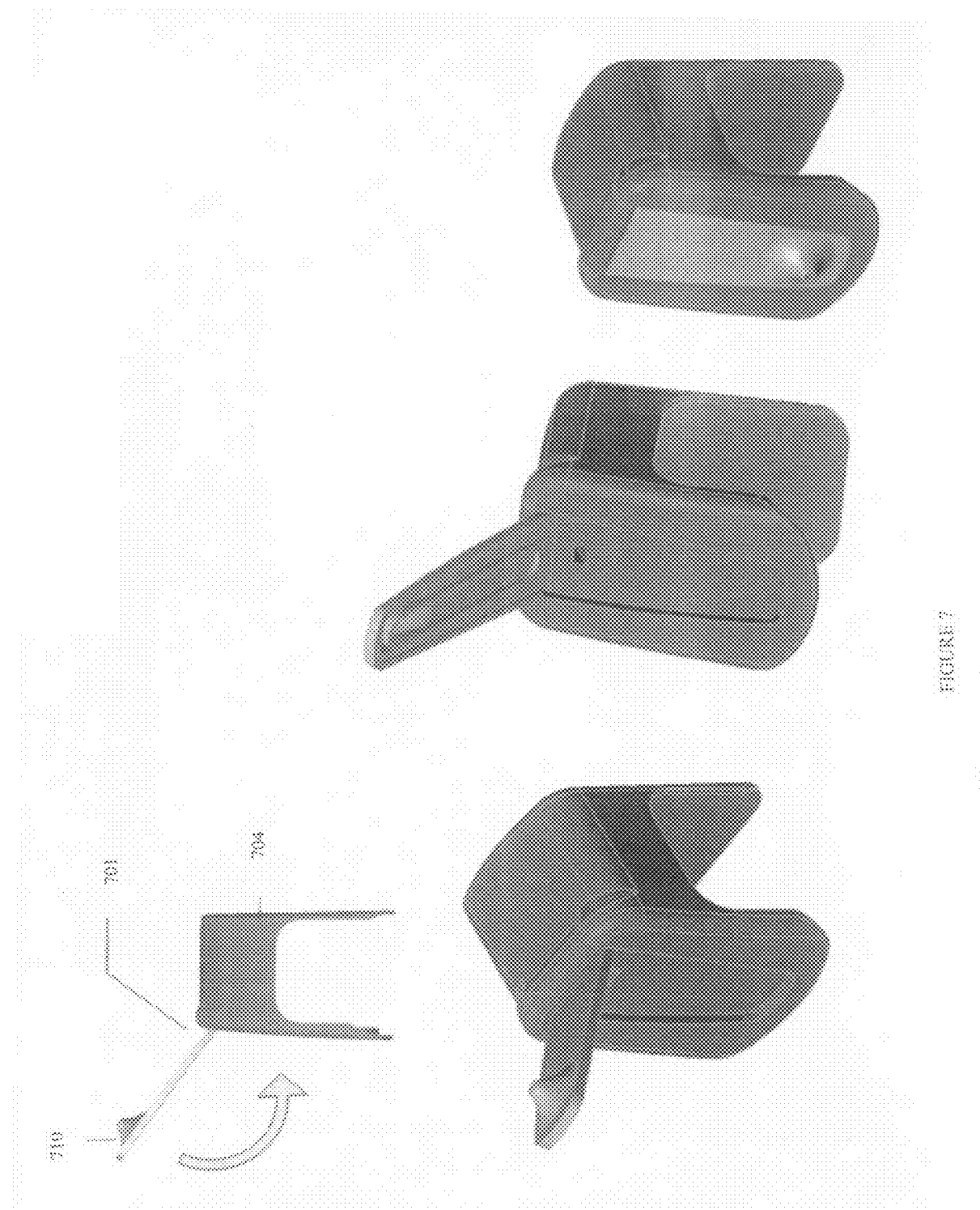
FIG. 7 shows an embodiment with an integrated one piece overcap with gel redirect "piping route" allowing gel to dispense in palm of users hand including wherein a redirect piping piece is integrally formed in the body of overcap with a hinge which allows snapping the piping piece into the main body of the overcap.

In another embodiment, the fluid dispenser further comprises an overcap button attached to the pumping unit, wherein the overcap button comprises a redirecting nozzle and an orifice which provides the aperture for dispensing the fluid from the receptacle when the button is actuated and the receptacle is unlocked, for example in a flipped down position. FIG. 7 shows an embodiment with an integrated one piece overcap with gel redirect "piping route" allowing gel to dispense in the palm of the user's hand. A redirect piping piece is integrally formed in the body of overcap with a hinge which allows snapping the piping piece into the main body of the overcap during assembly of the dispenser.

In yet another embodiment the clip is attached to the receptacle through a hinge allowing the receptacle to be positioned in an upright or a flipped down position and the clip further comprises a bottle retaining portion which allows the receptacle to be secured and locked in the upright position.

In yet another embodiment the dispenser comprises a swivel body formed by the receptacle, the pumping unit and the overcap button, the swivel body being attached to the clip by a hinge integrally molded to the clip, whereby a user releases the swivel body from the upright position by pulling the swivel body away from the clip.

In a further embodiment the hinge mechanism and button are positioned to allow one-hand-action of the dispenser in rapid sequence through an unlocking of the dispensing function, a dispensing function, and a relocking of the dispensing function.

In a further embodiment, the hinge mechanism and button are positioned to allow a locked state wherein dispensation of fluid is substantially impeded and an unlocked state wherein dispensation is facilitated, wherein a user can switch between the locked and unlocked states with a one-hand-action sequence within two seconds or less.

In still another embodiment, a retaining portion is positioned in the clip to lock the dispenser and prevent accidental discharge of fluid from the receptacle when the receptacle is in an upright position.

In yet a further embodiment, the receptacle comprises a hollow plastic component with threads to secure the pumping unit, threads to guide an overcap button in its travel, and threads to provide an angle-stopping feature when the receptacle is mated to the clip. The overcap includes a hinge (801) that is a one-piece living hinge that may be flipped down and then the one side RF or ultrasonically welded during assembly of the device.

In some embodiments, the maximum open angle (for maximal dispensation) is determined by an "angle-determining" feature on the clip component.

Figure 8:
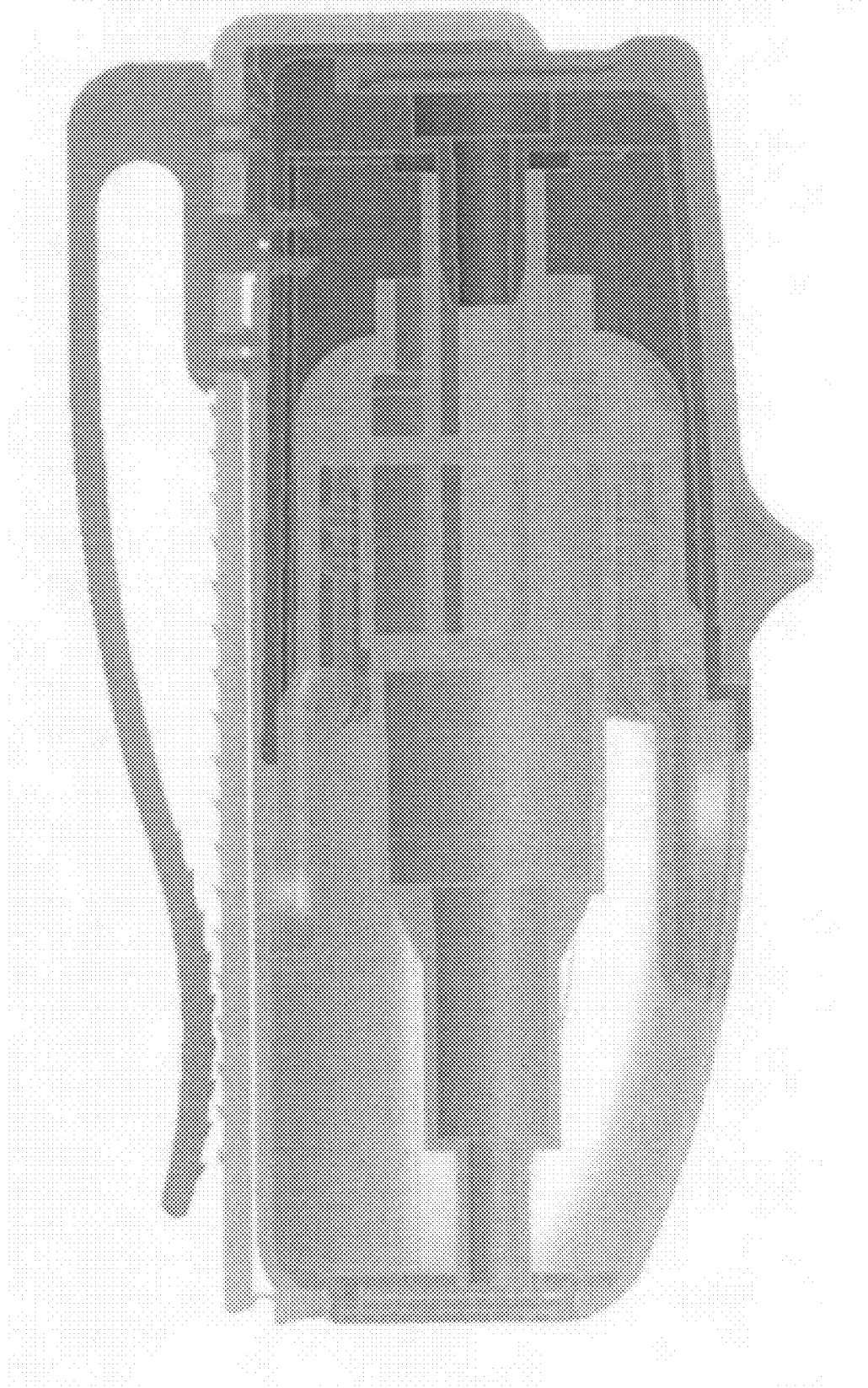
FIG. 8 shows Gel flow diagram for one design embodiment using "overcap" attached to pump, gel is able to be redirected to dispense directly onto palm of users hand while in flipped-down position.

FIG. 8 shows gel flow diagram for one design embodiment using "overcap" attached to a pump. Antiseptic agent, for example a gel is able to be redirected to dispense directly onto palm of a user's hand while in unlocked position, for example in a flipped-down position. Several alternative methods to locking the unit in an upright position are contemplated herein. One embodiment illustrated in FIG. 8 employs a spring clip that engages in a hole in the back of the overcap. FIG. 8 shows a locking mechanism including forks that retain the bottle locked to the clip. The bottle is designed with recesses that allow the forks to snap into the recess and hold the bottle. When the bottle is pulled away from the clip, the forks are released from the recess and the bottle is unlocked. FIG. 8 also shows features in the clip which allow for hinge movement of the bottle. The attachment of the bottle at the bottom of the clip is releasable to allow for replacing an empty bottle with a new bottle containing the antiseptic agent. The retaining features at the bottom of the clip are disposed in way that allows control of the maximum angle of pivot for the bottle when it is in an unlocked position (e.g., the top locking forks are disengaged from the recesses in the bottle, while the bottom retaining features remain mated to the bottle.

Another embodiment employs a horizontally oriented collar-shaped clip, integrally connected to the clip body, which engages around the neck of the bottle or the pump, holding it upright, and preventing the button from being pushed down.

This mechanism acts to simultaneously hold the bottle in upright position and as a button-stop, preventing accidental dispensation.

FIG. 9 shows an embodiment with an additional clip component which attaches to a belt clip to allow the dispenser to be attached to the clothing of a user without the need for a belt. The dispenser illustrated in the figure allows dual use with and without a belt.

Figure 10:
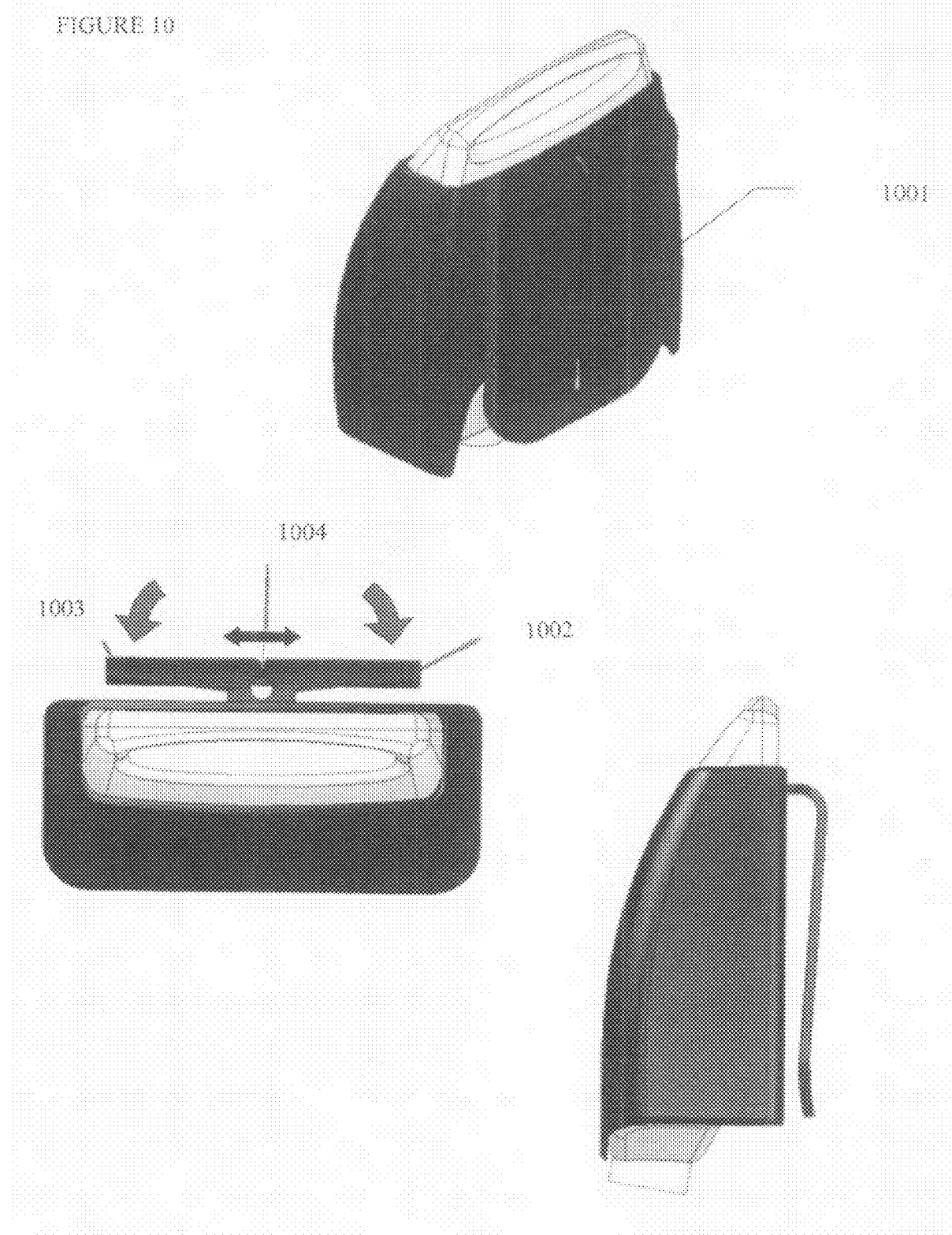
FIG. 10 shows an embodiment wherein the clip includes a slit for fabric retention. The embodiment shown in the figure allows for increasing the width of the slit by pressing either or both of two regions positioned opposite each other from a vertical slit, the pushing is stopped once a piece of the user's clothing is positioned into the slit.

FIG. 10 shows an embodiment wherein the clip includes a slit for fabric retention. The embodiment shown in the figure allows for increasing the width of the slit by pressing two regions positioned opposite each other from a vertical slit, the pushing is stopped once a piece of the user's clothing is positioned into the slit. The slit closes on the closing thereby allowing for clipping the dispenser to the user's clothing. In order to release the dispenser from the clothing, the user presses the body of the clip on the sides of the slit which opens the slits sufficiently to allow the user to disengage the piece of clothing from the dispenser.

FIG. 11 shows an embodiment incorporating a garment clip including a flap connected through a hinge to the main body of the clip whereby clothing of the user is positioned in the clip with the flap open, and snapping the flap closed allows for retention of the clip with the dispenser on the clothing of the user.

FIG. 12 shows an integrated clip and bottle for an entirely disposable dispenser. The dispenser includes a molded flexible compressible region which allows the user to dispense antiseptic agent by pressing on the flexible portion.

Figure 13:
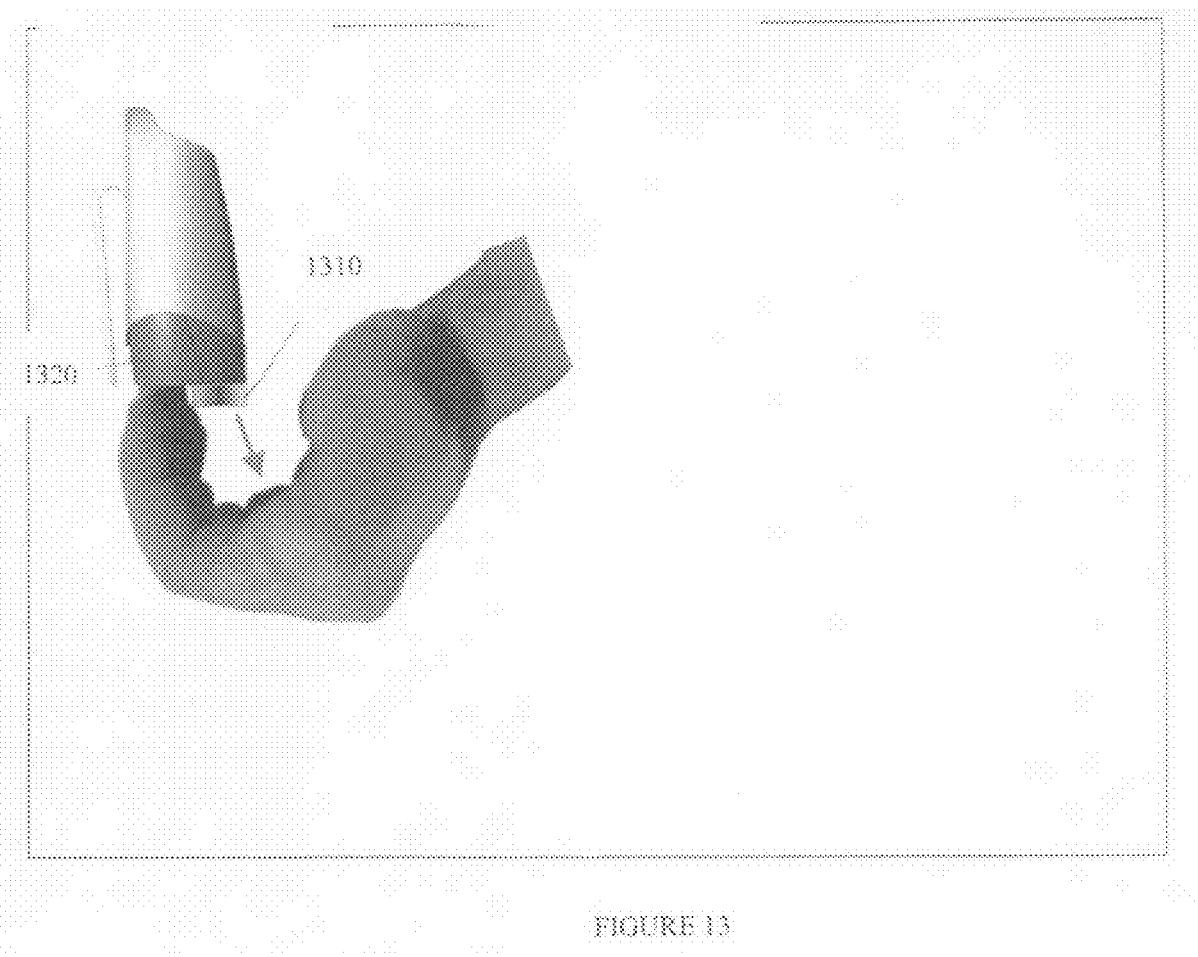
FIG. 13 illustrates an embodiment using the dispenser of FIG. 11.

FIG. 13 illustrates an embodiment using the dispenser of FIG. 12.

Another aspect provides a dispenser designed for the dispensing of antiseptic or antibacterial hand gels (hand sanitizers). In this aspect, the dispenser is roughly the size of a small cell-phone, and can be worn on an integral belt-clip. In one embodiment, the dispenser is designed as a reusable holster with a disposable cartridge. In some embodiments, the design is adapted to become fully disposable or fully reusable.

Figure 14:
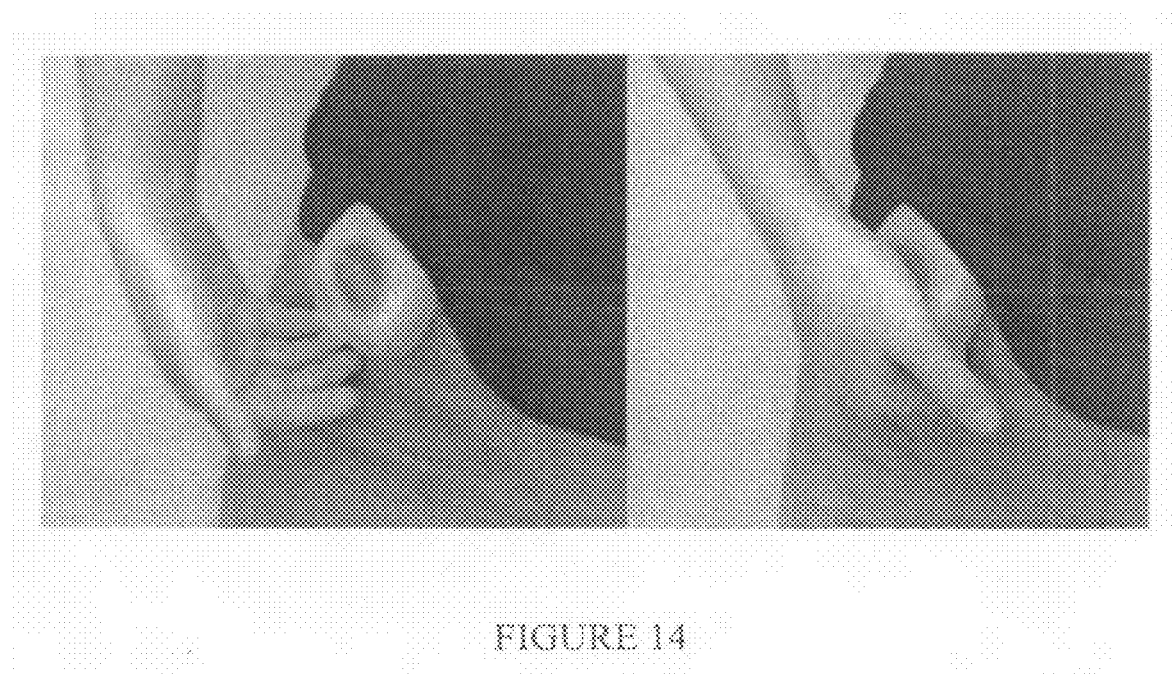
FIG. 14 shows operation of the dispenser of FIG. 13 wherein the user applies pressure to the cartridge (e.g. squeezes the bottle), gel dispenses onto the palm of the user's hand by way of increased pressure within the bottle resulting in the silicone valve opening and gel dispensing downwards.

FIG. 14 shows operation of the dispenser wherein the user applies pressure to the cartridge (e.g. squeezes the bottle), gel dispenses onto the palm of the user's hand by way of increased pressure within the bottle resulting in the silicone valve opening and gel dispensing downwards.

In one embodiment antiseptic gel is dispensed from the bottom of the unit by way of a squeeze bottle/flexible valve assembly, arranged to ensure that fluid dispenses neatly onto an appropriate part of the users' hand, allowing for commencement of proper hand hygiene. These ergonomic features expedite and enhance hand hygiene among caregivers.

FIGS. 12A and 12B show an integrated clip and bottle for an entirely disposable dispenser. FIG. 12A shows a loop (1301) at the top for attachment of a lanyard or necklace to the device. The dispenser shown in FIG. 12B includes a molded flexible compressible region (1202) which allows the user to dispense antiseptic agent by pressing on the flexible portion to allow the exiting of antiseptic gel through a silicone valve in the nozzle (1210).

FIG. 13 describes the use of the dispenser shown in FIG. 12. The fingers of the user fit underneath the unit and the palm of the user may make contact with the front of the unit. The fingers squeeze the flexible area (1320) of the unit causing gel to exit out of the bottom nozzle (1310) and silicone valve. Upon release of the flexible area, the finger squeeze bellows return to the original position (1-2 seconds) allowing the user to perform another dispense of gel.

In one embodiment, the unit is designed so that during normal use it would not accidentally dispense. This can be achieved for example through a hard plastic outer shell. If a user bends over, leans over, or accidentally bumps up against other objects, the antiseptic agent would not accidentally dispense.

In one embodiment, the bottle is made of materials that are flexible and allow the bottle to be squeezed to release the antiseptic agent through a valve mechanism. In another embodiment the holster is made of material that is less flexible than the material of the bottle so that pressure applied accidentally on the holster does not transfer to the bottle and accidental dispensing of the antiseptic agent is avoided. In this embodiment, the user applies pressure on the holster walls, for example by affecting a squeeze so that pressure is applied to the bottle and antiseptic agent is released.

In one embodiment a bottle in the form of a pouch, for example an IV bag is employed.

In one embodiment, the holster portion is made up of a relatively rigid material, for instance molded plastic, and thus protects a soft inner bottle from becoming accidentally bumped or squeezed, resulting in unwanted dispensing of gel. In this embodiment, a combination of a reusable, rigid outer case to disposable soft inner cartridge in a wearable alcohol gel dispenser provides a dispenser which achieves the objectives discussed above.

The holster portion may be worn in many different ways. Some embodiments are described herein.

The unit includes a holster and a cartridge that inserts into the holster. The holster may include ears molded into the body of the holster to retain the cartridge within the holster. The holster has tears on both sides inside the holster that bend outwards to accept the cartridge. Upon full insertion of the cartridge, the ears pop back into the default position. Shoulders on the tears (undercuts in mold) retain the cartridge inside the holster during use.

Figure 16:
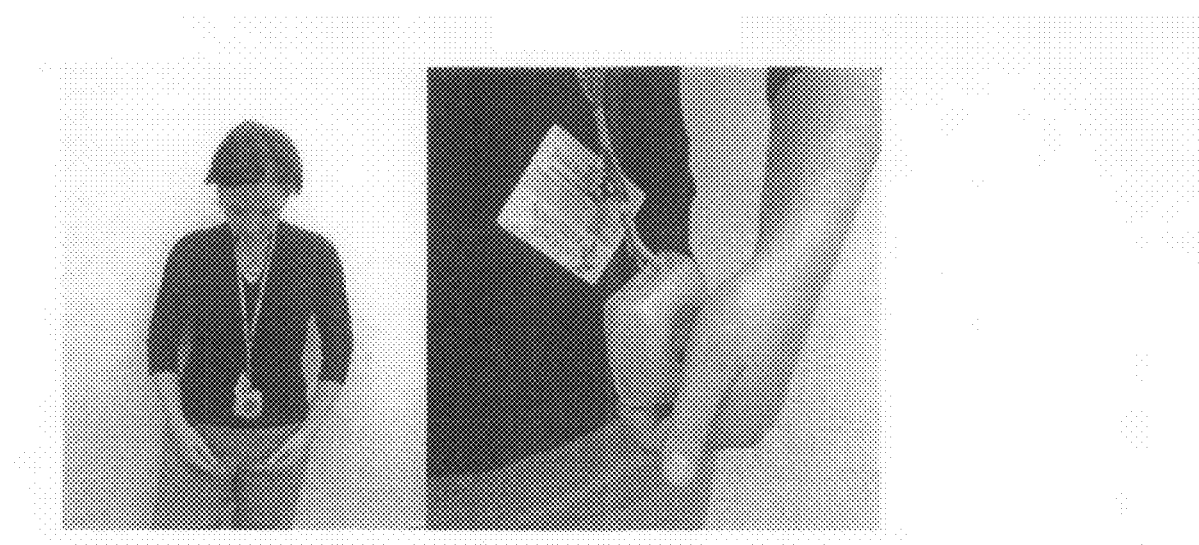
FIG. 16 illustrates an embodiment wherein the dispenser is attached to a necklace that can be worn be the user (in medical instances referred to as a lanyard).
Figure 15:
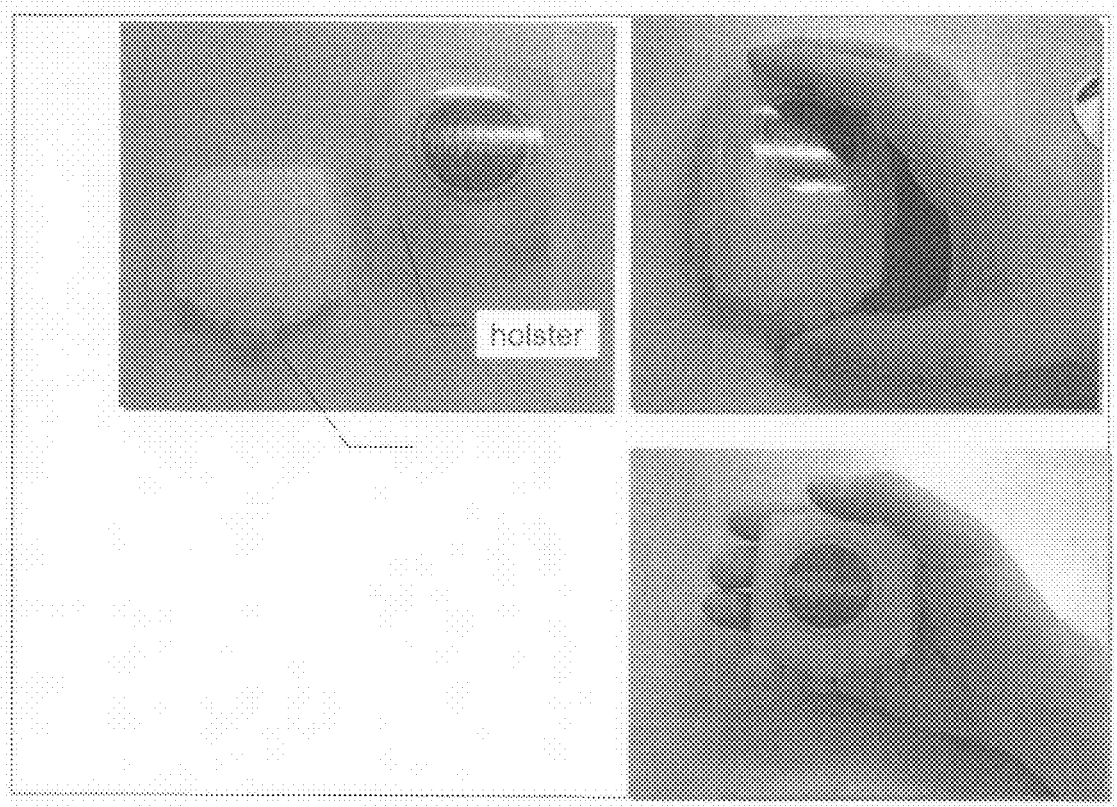
FIG. 15 illustrates how the cartridge is inserted with an integral nozzle facing downwards. The nozzle operates by way of a valve apparatus (for example, an economical elastomeric silicone valve).

Other contemplated embodiments include, without limitation, proper use and function of the dispenser provided herein while the dispenser is attached to a necklace that can be worn by the user (in medical instances referred to as a lanyard). These are commonly found in healthcare environments, and are used often to hold keys or ID badges. FIG. 16 illustrates an embodiment wherein the dispenser is attached to a necklace that can be worn by the user.

Another aspect provides a mechanism for attaching the dispenser to other clothing articles. In one embodiment, an otherwise-typical belt clip is designed to alternatively function as a cloth clip, where the unit may attach to, for instance, an overhanging piece of fabric such as a long shirt that has not been tucked in. FIG. 17 illustrates a mechanism for attaching the dispenser to other clothing articles.

An exemplary embodiment employs a 2-part design to attach the dispenser to a clothing item. The 2-part design includes a holster and a "plug" component.

FIG. 18 illustrates an exemplary embodiment employs a 2-part design to attach the dispenser to a clothing item. The 2-part design includes a holster with a cutout portions. The cutout portion can be circular, square or any other form. The second component is a "plug" component which fits in and covers the cutout portion in the holster, for example through a snapping mechanism. The holster and the plug sandwich a piece of fabric from the user clothing, thereby attaching the dispenser to the clothing of the user.

For example, an open part or cutout is formed in the back of the holster. The holster with the bottle placed therein is disposed on the external surface of the clothing of the user. The plug is placed on the internal surface of the clothing and snapped into the open part (cut out) formed in the back of the holster. In some embodiments, the plug may include holes that facilitate manipulation and placement on the holster with the fabric of the clothing of the user sandwiched between the plug and the main body of the holster.

Providing a dispenser that can be attached in a variety of locations on the clothing of the user provides highly desirable features, particularly in clinical settings, because many caregivers do not wear clothing that is compatible with a belt-clip, and that having such a design that can simply attach to a piece of fabric in a manner such as described herein would be very desirable.

FIG. 19 illustrates how the buttons in a one piece holster are pressed to release cartridge.

An embodiment based on employing a pin to attach the dispenser to the clothing of the user is contemplated herein.

Figures 19A, 19B:
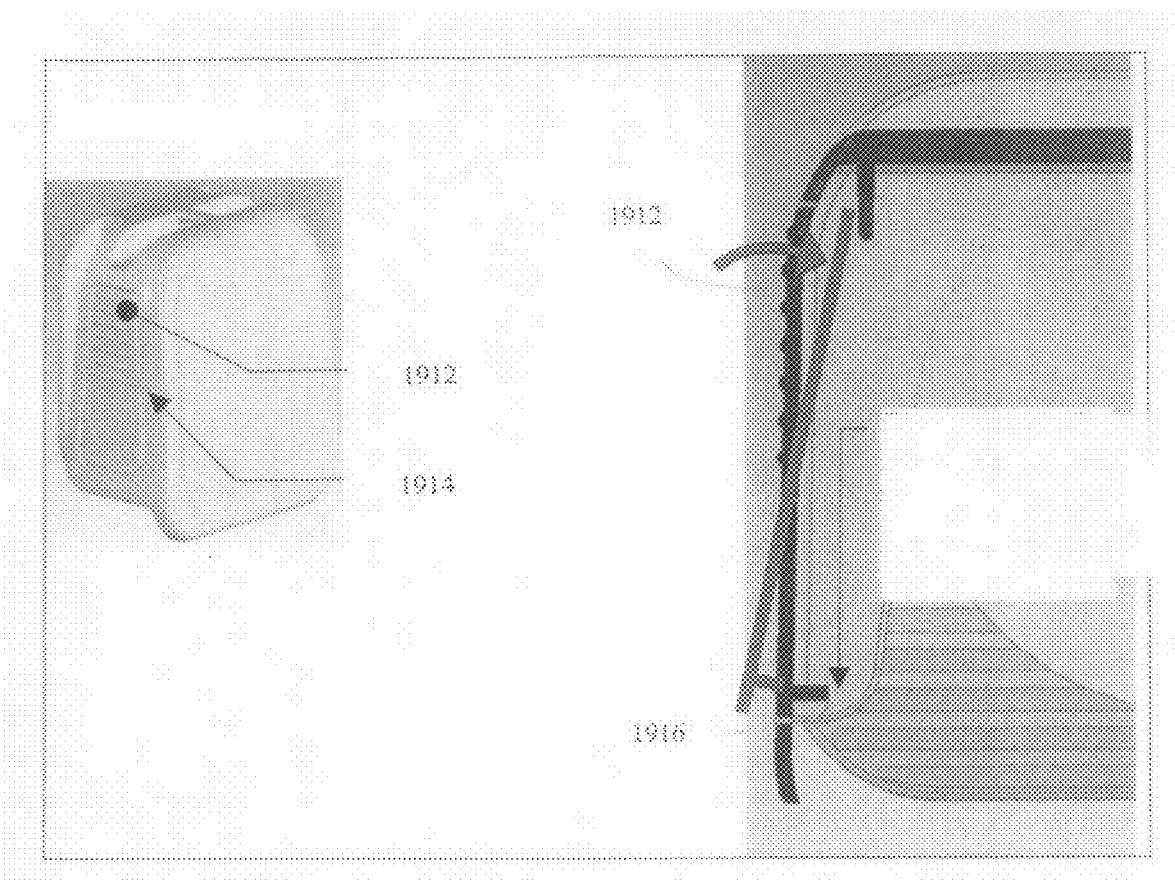
FIG. 19 illustrates how the buttons in a one piece holster according to FIG. 21 are pressed to release cartridge.
Figure 20:
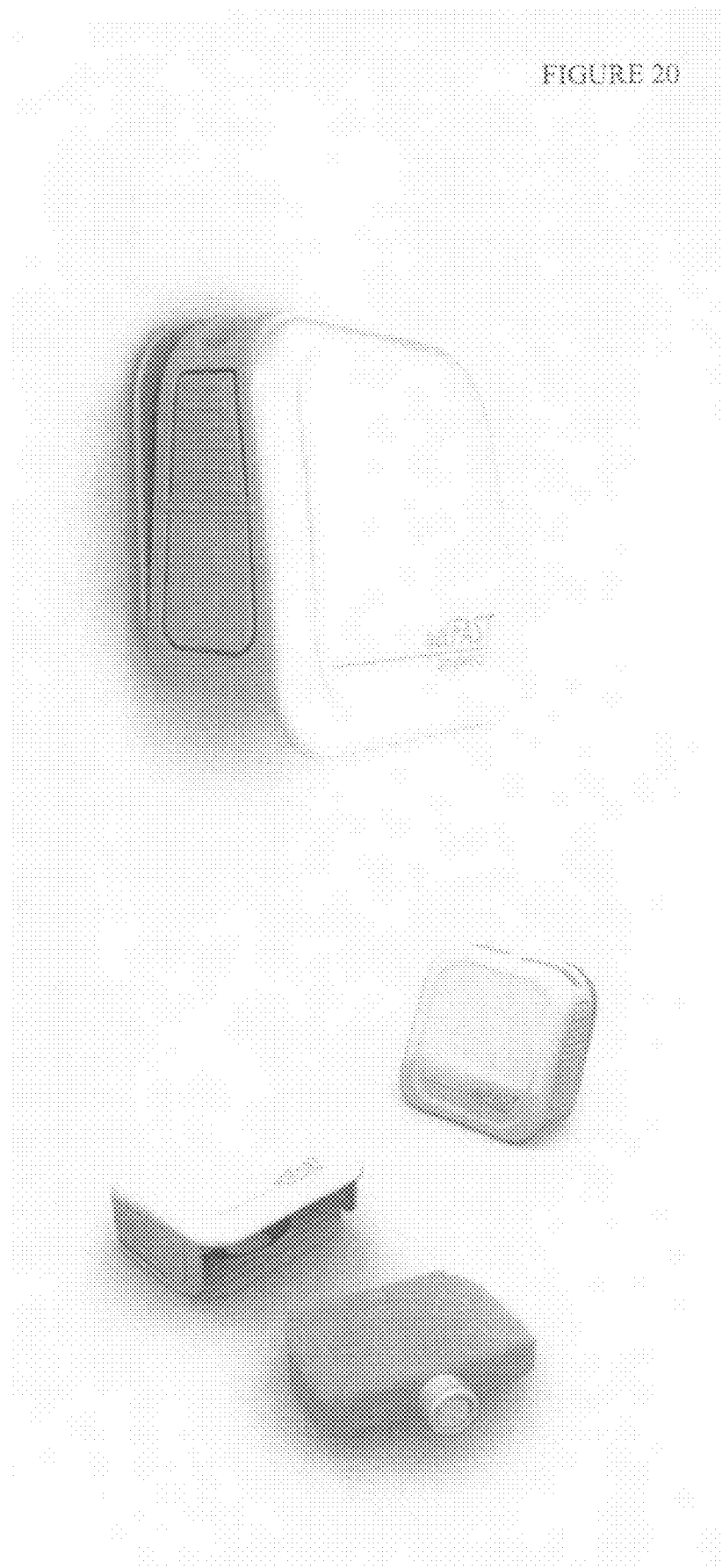
FIG. 20 illustrates a one piece dispenser with and without a bottle inserted in the holster.

FIG. 20 illustrates a one piece dispenser according FIG. 19 with and without a bottle inserted in the holster.

FIG. 21 illustrates a dispenser with the attachment mechanism illustrated in FIG. 18.

For certain instances where a typical belt-clip is not sufficient to withstand the rigors of more demanding environments, such as emergency response or law enforcement personnel, a fitting that allows for the unit to be securely threaded through a work-belt as is typically found in those environments is also contemplated.

FIG. 19A shows the unit with two buttons (1912) on each side of the unit. The two buttons when pressed or pushed at the same time release the cartridge from the bottom of the unit. The region (1914) or material below the button (1912) acts like a small hinge. FIG. 19B shows the interior of the holster and the mechanism for retention and release of the cartridge from the holster. Pressing the button (1912) at the top causes the material to act like a small hinge so that the bottom recedes along with the ears (1916) allowing the cartridge to be removed from the bottom of the holster.

Another aspect provides a soft fabric holster, similar to a sewn cell-phone holster that has a reinforcing plate inside (the plate can be made of metal, plastic or other material) which serves to prevent accidental squeezing and dispensing of the unit. This fabric holster would accept cartridges in a similar way to the plastic holster discussed above. The primary difference here is that the unit may be more durable for the more extreme environments of law enforcement or emergency response personnel.

Embodiments wherein the wearable unit may be adapted for use in many other situations which do not require attachment to a clothing item of the user are also contemplated. For example, and without limitation, the following applications are envisaged for certain embodiments of the dispenser disclosed herein. Attachment mechanisms and situations include employing a small magnetic fitting which allows unit to be temporarily affixed to metallic surfaces such as refrigerator doors. A Velcro-style adhesive-backed fitting that allows unit to be temporarily affixed to other surfaces, such as automobile dashboards, walls, or many other objects is also contemplated.

Figure 21A:
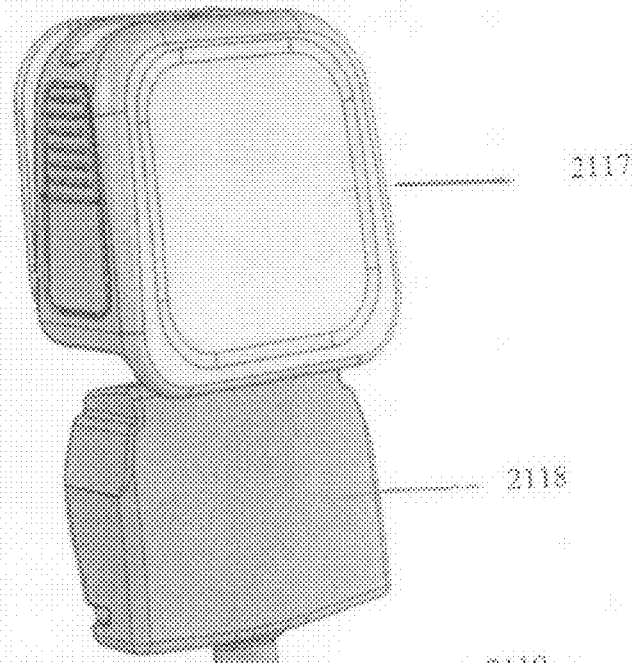
FIG. 21 illustrates a dispenser as shown in FIGS. 18 and 19 with the attachment mechanism illustrated in FIG. 17.
Figure 21B:
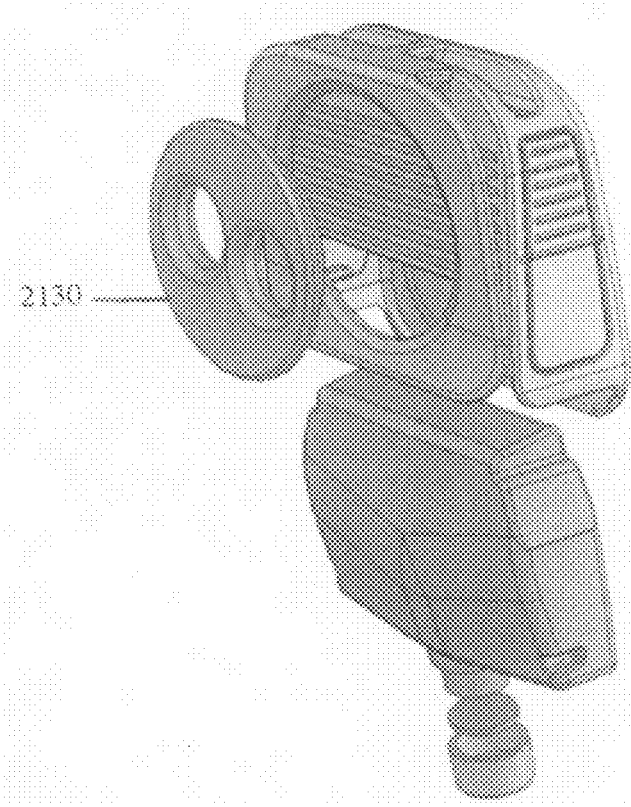

FIG. 21A illustrates the holster (2117) and removable flexible cartridge (2118) having a nozzle (2110) for dispensing antiseptic gen through a silicone valve (2119). The rear of the unit is illustrated in FIG. 21B showing a removable plug (2130) which may be utilized for attachment of the unit to fabric or clothing of the user.

Figure 22:
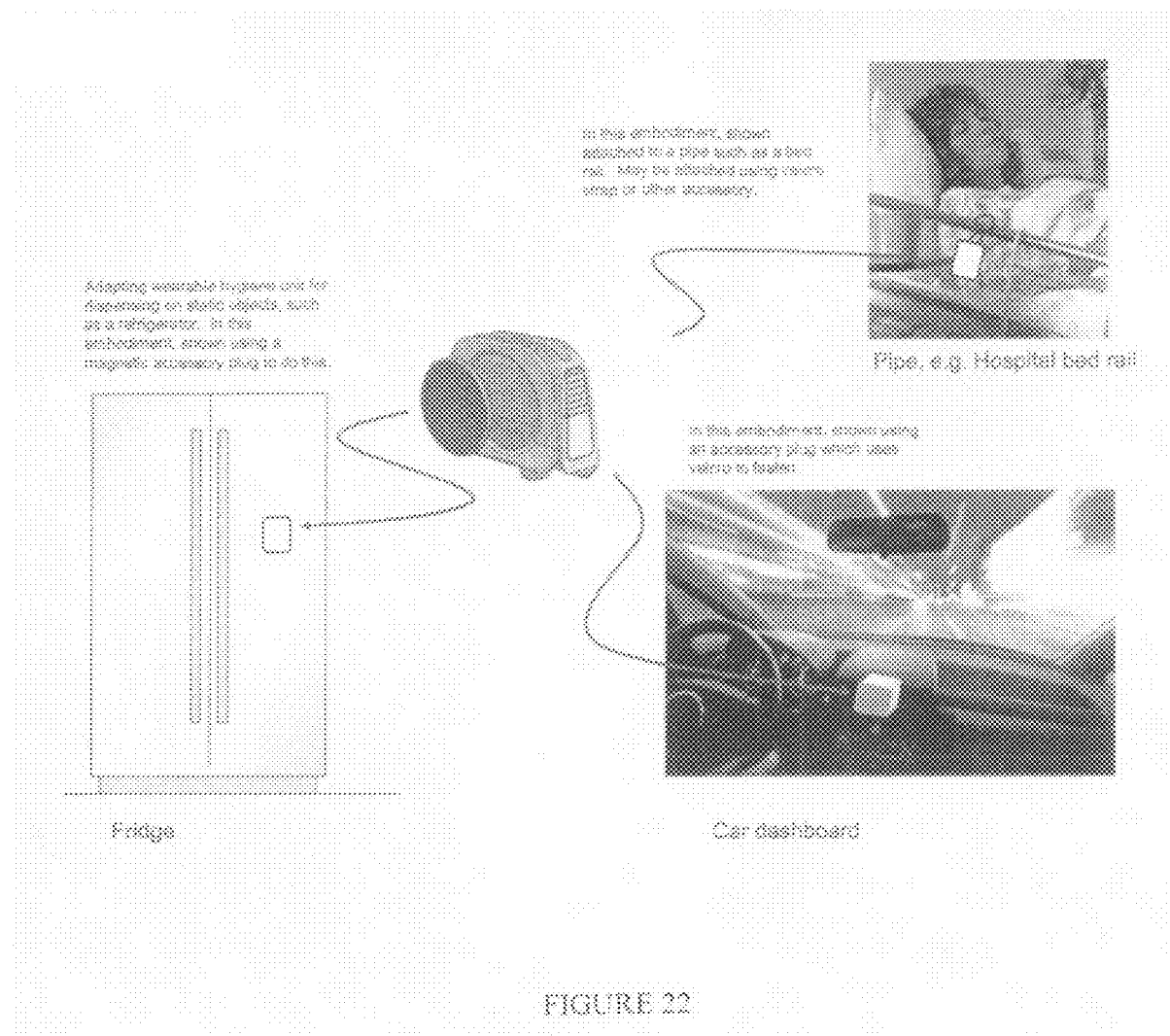
FIG. 22 illustrates attachment mechanisms and situations including employing a small magnetic fitting which allows unit to be temporarily affixed to metallic surfaces such as refrigerator doors. A Velcro-style adhesive-backed fitting that allows unit to be temporarily affixed to other surfaces, such as automobile dashboards, walls, or many other objects is also contemplated.

FIG. 22 illustrates attachment mechanisms and situations including employing a small magnetic fitting which allows unit to be temporarily affixed to metallic surfaces such as refrigerator doors.

One aspect relates to a valve that can be fitted or snapped into the neck of a bottle without a need for additional seal. In one embodiment this achieved by molding the valve in a single piece having a geometry including a valve membrane disposed between two lead-in portions. The leading portion include angled or radial portions and lip portions which allow the valve to be secured the neck of a bottle. The valve include U shaped portions with a buffer space separating the membrane portion from the lead-in portions thereby allowing the high tolerance elastomeric valve to snap into a low tolerance low precision bottle neck.

The membrane comprises one or more slits which allow the antiseptic agent to be dispensed through the valve when the bottle is pressed. In the absence of the pressure exerted on the walls of the bottle, the antiseptic agent is not discharged through the valve. When sufficient pressure is exerted, the antiseptic agent is discharged through the slit system formed by one or more slits.

FIG. 23 depicts a valve which snaps into the neck of a bottle without the need for additional seal disposed between the neck of the bottle and the valve FIG. 24 illustrates how the valve is directly disposed in the neck of the bottle.

What is claimed is:

1. A wearable fluid dispenser comprising a reusable holster and a disposable cartridge for providing a fluid, wherein the cartridge is made of material having a flexibility higher than the flexibility of the holster, and wherein applying pressure to the cartridge allows dispensing said fluid onto the palm of a user's hand by way of increased pressure within the cartridge resulting in fluid dispensing downwards, wherein the holster comprises a cutout portion that can be closed with a plug, wherein the dispenser can be attached to the user's clothing by positioning a piece of clothing between the cutout portion and the plug.

2. A wearable fluid dispenser comprising a reusable holster and a disposable cartridge for providing a fluid, wherein the cartridge is made of material having a flexibility higher than the flexibility of the holster, and wherein applying pressure to the cartridge allows dispensing said fluid onto the palm of a user's hand by way of increased pressure within the cartridge resulting in fluid dispensing downwards, wherein the holster is a plastic holster having two buttons which when depressed simultaneously allow release of the cartridge for replacement while preventing accidental release of the cartridge when in use.

3. The dispenser of claim 2, wherein the cartridge comprises a valve fitted into a neck of said cartridge.

4. The dispenser of claim 3, wherein said valve comprises a membrane disposed between two lead-in portions.

5. The dispenser of claim 4, wherein the lead-in portions have angled or radial portions and lip portions which allow the valve to be secured to the neck of the cartridge.

6. The dispenser of claim 5, wherein the valve comprises a U shaped portion which provides a buffer space separating the membrane portion from the lead-in portions thereby allowing a high tolerance elastomeric valve to snap into a low tolerance low precision cartridge neck.

7. The dispenser of claim 6 wherein the membrane comprises one or more slits which allow fluid in the cartridge to be dispensed through the valve when the cartridge is pressed.

8. The dispenser of claim 2, wherein said fluid is antiseptic agent.

9. The dispenser of claim 2, wherein said fluid is antiseptic agent containing alcohol.

10. The dispenser of claim 2, wherein the fluid is antiseptic gel.

11. The dispenser of claim 2, wherein the fluid is antiseptic gel containing 40% alcohol.

12. The dispenser of claim 2, wherein the cartridge comprises an integral nozzle facing downwards when the dispenser is in position for dispensing said fluid.

13. The dispenser of claim 2, wherein the holster comprises ears molded in the body of said holster for locking said cartridge inside said holster.

14. The dispenser of claim 2, wherein the holster comprises a frame geometry that allows attachment of the holster to a necklace that can be worn by the user.

* * * * *